United States Patent
Fox et al.

(10) Patent No.: US 7,198,675 B2
(45) Date of Patent: Apr. 3, 2007

(54) STENT MANDREL FIXTURE AND METHOD FOR SELECTIVELY COATING SURFACES OF A STENT

(75) Inventors: Jason Fox, Milpitas, CA (US); Nathan Harold, Santa Clara, CA (US); Barry Templin, Milpitas, CA (US); Andrew Tochterman, Milpitas, CA (US)

(73) Assignee: Advanced Cardiovascular Systems, Santa Clara, CA (US)

( * ) Notice: Subject to any disclaimer, the term of this patent is extended or adjusted under 35 U.S.C. 154(b) by 294 days.

(21) Appl. No.: 10/676,545

(22) Filed: Sep. 30, 2003

(65) Prior Publication Data

US 2005/0069630 A1    Mar. 31, 2005

(51) Int. Cl.
B05C 13/02 (2006.01)

(52) U.S. Cl. .................. 118/500; 118/504; 118/505; 623/1.46; 623/1.47; 623/1.48

(58) Field of Classification Search .............. 118/500, 118/504, 505; 427/2.24, 2.25, 2.28, 2.3; 623/1.46, 1.47, 1.48, 1.1; 606/192, 198, 606/194, 108

See application file for complete search history.

(56) References Cited

U.S. PATENT DOCUMENTS

| 2,072,303 | A | 3/1937 | Herrmann et al. |
|---|---|---|---|
| 2,386,454 | A | 10/1945 | Frosch et al. |
| 2,647,017 | A | 7/1953 | Coulliette |
| 2,701,559 | A | 2/1955 | Cooper |
| 3,288,728 | A | 11/1966 | Gorham |
| 3,687,135 | A | 8/1972 | Stroganov et al. |
| 3,773,737 | A | 11/1973 | Goodman et al. |
| 3,839,743 | A | 10/1974 | Schwarcz |
| 3,849,514 | A | 11/1974 | Gray, Jr. et al. |
| 3,900,632 | A | 8/1975 | Robinson |
| 4,075,045 | A | 2/1978 | Rideout |
| 4,104,410 | A | 8/1978 | Malecki |
| 4,110,497 | A | 8/1978 | Hoel |
| 4,132,357 | A | 1/1979 | Blackinton |
| 4,164,524 | A | 8/1979 | Ward et al. |
| 4,226,243 | A | 10/1980 | Shalaby et al. |
| 4,321,711 | A | 3/1982 | Mano |
| 4,323,071 | A | 4/1982 | Simpson et al. |
| 4,329,383 | A | 5/1982 | Joh |
| 4,338,942 | A | 7/1982 | Fogarty |

(Continued)

FOREIGN PATENT DOCUMENTS

CA    2 008 312    7/1990

(Continued)

OTHER PUBLICATIONS

Angioplasty.org., *Balloons and Stents*, http://www.ptca.org/devices04.html, printed Oct. 15, 2004, 2 pages.

(Continued)

*Primary Examiner*—Laura Edwards
(74) *Attorney, Agent, or Firm*—Squire Sanders & Dempsey

(57) ABSTRACT

A stent mandrel fixture for supporting a stent during the application of a coating substance is provided. A method supporting a stent during the application of a coating substance is also provided.

7 Claims, 4 Drawing Sheets

Unexpanded

Expanded

U.S. PATENT DOCUMENTS

| | | |
|---|---|---|
| 4,343,931 A | 8/1982 | Barrows |
| 4,346,028 A | 8/1982 | Griffith |
| 4,439,185 A | 3/1984 | Lundquist |
| 4,489,670 A | 12/1984 | Mosser et al. |
| 4,516,972 A | 5/1985 | Samson |
| 4,529,792 A | 7/1985 | Barrows |
| 4,538,622 A | 9/1985 | Samson et al. |
| 4,554,929 A | 11/1985 | Samson et al. |
| 4,573,470 A | 3/1986 | Samson et al. |
| 4,596,574 A | 6/1986 | Urist |
| 4,599,085 A | 7/1986 | Riess et al. |
| 4,608,984 A | 9/1986 | Fogarty |
| 4,611,051 A | 9/1986 | Hayes et al. |
| 4,612,009 A | 9/1986 | Drobnik et al. |
| 4,616,593 A | 10/1986 | Kawamura et al. |
| 4,616,652 A | 10/1986 | Simpson |
| 4,629,563 A | 12/1986 | Wrasidlo ............ 210/500.34 |
| 4,633,873 A | 1/1987 | Dumican et al. |
| 4,638,805 A | 1/1987 | Powell |
| 4,656,083 A | 4/1987 | Hoffman et al. |
| 4,656,242 A | 4/1987 | Swan et al. |
| 4,699,611 A | 10/1987 | Bowden |
| 4,702,252 A | 10/1987 | Brooks et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallsten et al. |
| 4,733,665 A | 3/1988 | Palmaz ............ 128/343 |
| 4,739,762 A | 4/1988 | Palmaz |
| 4,740,207 A | 4/1988 | Kreamer |
| 4,743,252 A | 5/1988 | Martin, Jr. et al. |
| 4,748,982 A | 6/1988 | Horzewski et al. |
| 4,762,128 A * | 8/1988 | Rosenbluth ............ 606/192 |
| 4,768,507 A | 9/1988 | Fischell et al. |
| 4,774,039 A | 9/1988 | Wrasidlo |
| 4,776,337 A | 10/1988 | Palmaz |
| 4,800,882 A | 1/1989 | Gianturco ............ 128/343 |
| 4,816,339 A | 3/1989 | Tu et al. |
| 4,818,559 A | 4/1989 | Hama et al. |
| 4,828,561 A | 5/1989 | Woodroof |
| 4,850,999 A | 7/1989 | Planck |
| 4,865,870 A | 9/1989 | Hu et al. |
| 4,871,542 A | 10/1989 | Vilhardt |
| 4,877,030 A | 10/1989 | Beck et al. |
| 4,878,906 A | 11/1989 | Lindemann et al. |
| 4,879,135 A | 11/1989 | Greco et al. |
| 4,880,683 A | 11/1989 | Stow |
| 4,882,168 A | 11/1989 | Casey et al. |
| 4,886,062 A | 12/1989 | Wiktor ............ 128/343 |
| 4,902,289 A | 2/1990 | Yannas |
| 4,906,423 A | 3/1990 | Frisch ............ 264/48 |
| 4,931,287 A | 6/1990 | Bae et al. |
| 4,932,353 A | 6/1990 | Kawata et al. |
| 4,941,870 A | 7/1990 | Okada et al. |
| 4,943,346 A | 7/1990 | Mattelin |
| 4,950,227 A | 8/1990 | Savin et al. |
| 4,955,899 A | 9/1990 | Della Corna et al. |
| 4,967,606 A | 11/1990 | Wells et al. |
| 4,977,901 A | 12/1990 | Ofstead |
| 4,988,356 A | 1/1991 | Crittenden et al. |
| 4,994,033 A | 2/1991 | Shockey et al. |
| 4,994,298 A | 2/1991 | Yasuda |
| 4,994,560 A | 2/1991 | Kruper, Jr. et al. |
| 5,015,505 A | 5/1991 | Cetnar |
| 5,019,090 A | 5/1991 | Pinchuk |
| 5,019,096 A | 5/1991 | Fox, Jr. et al. |
| 5,028,597 A | 7/1991 | Kodama et al. |
| 5,037,392 A * | 8/1991 | Hillstead ............ 606/194 |
| 5,037,427 A | 8/1991 | Harada et al. ............ 606/108 |
| 5,040,548 A | 8/1991 | Yock |
| 5,047,050 A | 9/1991 | Arpesani |
| 5,049,132 A | 9/1991 | Shaffer et al. |
| 5,053,048 A | 10/1991 | Pinchuk |
| 5,059,166 A | 10/1991 | Fischell et al. |
| 5,059,169 A | 10/1991 | Zilber |
| 5,059,211 A | 10/1991 | Stack et al. |
| 5,062,829 A | 11/1991 | Pryor et al. |
| 5,064,435 A | 11/1991 | Porter |
| 5,078,720 A | 1/1992 | Burton et al. |
| 5,081,394 A | 1/1992 | Morishita et al. |
| 5,084,065 A | 1/1992 | Weldon et al. |
| 5,085,629 A | 2/1992 | Goldberg et al. |
| 5,087,244 A | 2/1992 | Wolinsky et al. |
| 5,087,394 A | 2/1992 | Keith |
| 5,100,429 A | 3/1992 | Sinofsky et al. |
| 5,100,992 A | 3/1992 | Cohn et al. |
| 5,102,402 A | 4/1992 | Dror et al. |
| 5,104,410 A | 4/1992 | Chowdhary |
| 5,108,416 A | 4/1992 | Ryan et al. |
| 5,108,417 A | 4/1992 | Sawyer |
| 5,108,755 A | 4/1992 | Daniels et al. |
| 5,112,457 A | 5/1992 | Marchant |
| 5,116,318 A | 5/1992 | Hillstead |
| 5,116,365 A | 5/1992 | Hillstead |
| 5,123,917 A | 6/1992 | Lee |
| 5,127,362 A | 7/1992 | Iwatsu et al. |
| 5,133,742 A | 7/1992 | Pinchuk |
| 5,134,192 A | 7/1992 | Feijen et al. |
| 5,147,370 A | 9/1992 | McNamara et al. |
| 5,156,623 A | 10/1992 | Hakamatsuka et al. |
| 5,156,911 A | 10/1992 | Stewart |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,165,919 A | 11/1992 | Sasaki et al. |
| 5,167,614 A | 12/1992 | Tessmann et al. |
| 5,171,445 A | 12/1992 | Zepf ............ 210/500.27 |
| 5,176,638 A | 1/1993 | Don Michael |
| 5,188,734 A | 2/1993 | Zepf ............ 210/490 |
| 5,192,311 A | 3/1993 | King et al. |
| 5,197,977 A | 3/1993 | Hoffman, Jr. et al. |
| 5,205,822 A | 4/1993 | Johnson et al. |
| 5,213,561 A | 5/1993 | Weinstein et al. |
| 5,213,576 A | 5/1993 | Abiuso et al. |
| 5,219,980 A | 6/1993 | Swidler |
| 5,222,971 A | 6/1993 | Willard et al. |
| 5,225,750 A | 7/1993 | Higuchi et al. |
| 5,226,889 A | 7/1993 | Sheiban |
| 5,226,913 A | 7/1993 | Pinchuk |
| 5,229,045 A | 7/1993 | Soldani ............ 264/41 |
| 5,229,172 A | 7/1993 | Cahalan et al. |
| 5,232,444 A | 8/1993 | Just et al. |
| 5,234,456 A | 8/1993 | Silvestrini |
| 5,234,457 A | 8/1993 | Andersen ............ 606/198 |
| 5,236,447 A | 8/1993 | Kubo et al. |
| 5,242,399 A | 9/1993 | Lau et al. |
| 5,254,089 A | 10/1993 | Wang |
| 5,254,091 A | 10/1993 | Aliahmad et al. |
| 5,258,020 A | 11/1993 | Froix |
| 5,258,419 A | 11/1993 | Rolando et al. |
| 5,269,802 A | 12/1993 | Garber |
| 5,272,012 A | 12/1993 | Opolski |
| 5,278,200 A | 1/1994 | Coury et al. |
| 5,279,594 A | 1/1994 | Jackson |
| 5,282,823 A | 2/1994 | Schwartz et al. |
| 5,282,860 A | 2/1994 | Matsuno et al. |
| 5,286,254 A | 2/1994 | Shapland et al. |
| 5,289,831 A | 3/1994 | Bosley |
| 5,290,271 A | 3/1994 | Jernberg |
| 5,292,516 A | 3/1994 | Viegas et al. |
| 5,298,260 A | 3/1994 | Viegas et al. |
| 5,300,295 A | 4/1994 | Viegas et al. |
| 5,304,200 A | 4/1994 | Spaulding |

| Patent No. | Date | Inventor(s) | Ref |
|---|---|---|---|
| 5,306,250 A | 4/1994 | March et al. | |
| 5,306,286 A | 4/1994 | Stack et al. | |
| 5,306,294 A | 4/1994 | Winston et al. | |
| 5,306,501 A | 4/1994 | Viegas et al. | |
| 5,306,786 A | 4/1994 | Moens et al. | |
| 5,308,641 A | 5/1994 | Cahalan et al. | |
| 5,314,472 A | 5/1994 | Fontaine | |
| 5,318,531 A | 6/1994 | Leone | |
| 5,328,471 A | 7/1994 | Slepian | |
| 5,330,500 A | 7/1994 | Song | |
| 5,330,768 A | 7/1994 | Park et al. | |
| 5,336,518 A | 8/1994 | Narayanan et al. | |
| 5,342,283 A | 8/1994 | Good | |
| 5,342,348 A | 8/1994 | Kaplan | |
| 5,342,395 A | 8/1994 | Jarrett et al. | |
| 5,342,621 A | 8/1994 | Eury | |
| 5,344,426 A | 9/1994 | Lau et al. | |
| 5,344,455 A | 9/1994 | Keogh et al. | |
| 5,350,800 A | 9/1994 | Verhoeven et al. | |
| 5,356,433 A | 10/1994 | Rowland et al. | |
| 5,360,401 A | 11/1994 | Turnland et al. | |
| 5,360,443 A | 11/1994 | Barone et al. | |
| 5,363,881 A * | 11/1994 | Larkin | 138/89 |
| 5,364,354 A | 11/1994 | Walker et al. | |
| 5,366,504 A | 11/1994 | Andersen et al. | |
| 5,368,560 A | 11/1994 | Rambo et al. | |
| 5,370,684 A | 12/1994 | Vallana et al. | |
| 5,380,299 A | 1/1995 | Fearnot et al. | |
| 5,383,925 A | 1/1995 | Schmitt | |
| 5,383,927 A | 1/1995 | DeGoicoechea et al. | |
| 5,385,580 A | 1/1995 | Schmitt | |
| 5,387,450 A | 2/1995 | Stewart | |
| 5,389,106 A | 2/1995 | Tower | |
| 5,399,666 A | 3/1995 | Ford | |
| 5,405,472 A | 4/1995 | Leone | |
| 5,409,495 A | 4/1995 | Osborn | |
| 5,411,466 A | 5/1995 | Hess | |
| 5,411,477 A | 5/1995 | Saab | |
| 5,412,035 A | 5/1995 | Schmitt et al. | |
| 5,415,938 A | 5/1995 | Cahalan et al. | |
| 5,417,981 A | 5/1995 | Endo et al. | |
| 5,423,849 A | 6/1995 | Engelson et al. | |
| 5,423,885 A | 6/1995 | Williams | |
| 5,429,618 A | 7/1995 | Keogh | |
| 5,441,515 A | 8/1995 | Khosravi et al. | |
| 5,443,458 A | 8/1995 | Eury et al. | |
| 5,443,496 A | 8/1995 | Schwartz et al. | |
| 5,443,500 A | 8/1995 | Sigwart | |
| 5,445,646 A | 8/1995 | Euteneuer et al. | |
| 5,447,724 A | 9/1995 | Helmus et al. | |
| 5,451,233 A | 9/1995 | Yock | |
| 5,455,040 A | 10/1995 | Marchant | |
| 5,456,661 A | 10/1995 | Narciso, Jr. | |
| 5,456,713 A | 10/1995 | Chuter | |
| 5,458,615 A | 10/1995 | Klemm et al. | |
| 5,460,610 A | 10/1995 | Don Michael | |
| 5,462,990 A | 10/1995 | Hubbell et al. | |
| 5,464,450 A | 11/1995 | Buscemi et al. | |
| 5,464,650 A | 11/1995 | Berg et al. | |
| 5,470,313 A | 11/1995 | Crocker et al. | |
| 5,470,603 A | 11/1995 | Staniforth et al. | |
| 5,476,476 A | 12/1995 | Hillstead | |
| 5,476,509 A | 12/1995 | Keogh et al. | |
| 5,485,496 A | 1/1996 | Lee et al. | |
| 5,496,346 A | 3/1996 | Horzewski et al. | |
| 5,500,013 A | 3/1996 | Buscemi et al. | |
| 5,501,227 A | 3/1996 | Yock | |
| 5,502,158 A | 3/1996 | Sinclair et al. | |
| 5,507,768 A | 4/1996 | Lau et al. | |
| 5,511,726 A | 4/1996 | Greenspan et al. | |
| 5,514,154 A | 5/1996 | Lau et al. | |
| 5,514,379 A | 5/1996 | Weissleder et al. | |
| 5,516,560 A | 5/1996 | Harayama et al. | |
| 5,516,881 A | 5/1996 | Lee et al. | |
| 5,527,337 A | 6/1996 | Stack et al. | |
| 5,537,729 A | 7/1996 | Kolobow | 29/527.2 |
| 5,538,493 A | 7/1996 | Gerken et al. | |
| 5,545,209 A | 8/1996 | Roberts et al. | |
| 5,545,408 A | 8/1996 | Trigg et al. | |
| 5,551,954 A | 9/1996 | Buscemi et al. | |
| 5,554,120 A | 9/1996 | Chen et al. | |
| 5,554,182 A | 9/1996 | Dinh et al. | |
| 5,556,413 A | 9/1996 | Lam | |
| 5,558,642 A | 9/1996 | Schweich, Jr. et al. | |
| 5,562,728 A | 10/1996 | Lazarus et al. | |
| 5,569,463 A | 10/1996 | Helmus et al. | |
| 5,571,135 A | 11/1996 | Fraser et al. | |
| 5,571,166 A | 11/1996 | Dinh et al. | |
| 5,571,567 A | 11/1996 | Shah | |
| 5,578,046 A | 11/1996 | Liu et al. | |
| 5,578,048 A * | 11/1996 | Pasqualucci et al. | 606/192 |
| 5,578,073 A | 11/1996 | Haimovich et al. | |
| 5,584,877 A | 12/1996 | Miyake et al. | |
| 5,588,962 A | 12/1996 | Nicholas et al. | |
| 5,591,199 A | 1/1997 | Porter et al. | |
| 5,591,224 A | 1/1997 | Schwartz et al. | |
| 5,591,227 A | 1/1997 | Dinh et al. | |
| 5,591,607 A | 1/1997 | Gryaznov et al. | |
| 5,593,403 A | 1/1997 | Buscemi | |
| 5,593,434 A | 1/1997 | Williams | |
| 5,595,722 A | 1/1997 | Grainger et al. | |
| 5,599,301 A | 2/1997 | Jacobs et al. | |
| 5,599,307 A | 2/1997 | Bacher et al. | |
| 5,599,352 A | 2/1997 | Dinh et al. | |
| 5,599,922 A | 2/1997 | Gryaznov et al. | |
| 5,605,696 A | 2/1997 | Eury et al. | |
| 5,607,442 A | 3/1997 | Fischell et al. | |
| 5,607,467 A | 3/1997 | Froix | |
| 5,609,629 A | 3/1997 | Fearnot et al. | |
| 5,610,241 A | 3/1997 | Lee et al. | |
| 5,611,775 A | 3/1997 | Machold et al. | 604/53 |
| 5,616,338 A | 4/1997 | Fox, Jr. et al. | |
| 5,618,298 A | 4/1997 | Simon | |
| 5,618,299 A | 4/1997 | Khosravi et al. | |
| 5,620,420 A | 4/1997 | Kriesel | |
| 5,624,411 A | 4/1997 | Tuch | 604/265 |
| 5,628,730 A | 5/1997 | Shapland et al. | |
| 5,628,755 A | 5/1997 | Heller et al. | |
| 5,628,781 A | 5/1997 | Williams et al. | |
| 5,628,785 A | 5/1997 | Schwartz et al. | |
| 5,628,786 A | 5/1997 | Banas et al. | 623/1 |
| 5,629,077 A | 5/1997 | Turnlund et al. | |
| 5,631,135 A | 5/1997 | Gryaznov et al. | |
| 5,632,771 A | 5/1997 | Boatman et al. | |
| 5,632,840 A | 5/1997 | Campbell | |
| 5,637,113 A | 6/1997 | Tartaglia et al. | |
| 5,644,020 A | 7/1997 | Timmermann et al. | |
| 5,645,559 A | 7/1997 | Hachtman et al. | |
| 5,649,951 A | 7/1997 | Davidson | |
| 5,649,977 A | 7/1997 | Campbell | |
| 5,653,691 A | 8/1997 | Rupp et al. | |
| 5,656,080 A | 8/1997 | Staniforth et al. | |
| 5,656,082 A | 8/1997 | Takatsuki et al. | |
| 5,658,995 A | 8/1997 | Kohn et al. | |
| 5,667,523 A | 9/1997 | Bynon et al. | |
| 5,667,767 A | 9/1997 | Greff et al. | |
| 5,667,796 A | 9/1997 | Otten | |
| 5,670,558 A | 9/1997 | Onishi et al. | |
| 5,674,242 A | 10/1997 | Phan et al. | |
| 5,679,400 A | 10/1997 | Tuch | |
| 5,693,085 A | 12/1997 | Buirge et al. | |
| 5,693,376 A | 12/1997 | Fetherston et al. | |
| 5,695,498 A | 12/1997 | Tower | |
| 5,695,810 A | 12/1997 | Tower | |
| 5,697,967 A | 12/1997 | Dinh et al. | |
| 5,700,286 A | 12/1997 | Tartaglia et al. | |

| | | | | | |
|---|---|---|---|---|---|
| 5,702,754 A | 12/1997 | Zhong | 5,837,835 A | 11/1998 | Gryaznov et al. |
| 5,702,818 A | 12/1997 | Cahalan et al. | 5,840,009 A | 11/1998 | Fischell et al. |
| 5,707,385 A | 1/1998 | Williams | 5,840,083 A | 11/1998 | Braach-Maksvytis |
| 5,711,763 A | 1/1998 | Nonami et al. | 5,843,033 A | 12/1998 | Ropiak |
| 5,711,812 A | 1/1998 | Chapek et al. | 5,843,119 A | 12/1998 | Shulewitz |
| 5,711,958 A | 1/1998 | Cohn et al. | 5,843,172 A | 12/1998 | Yan |
| 5,713,949 A | 2/1998 | Jayaraman | 5,846,247 A | 12/1998 | Unsworth et al. |
| 5,716,981 A | 2/1998 | Hunter et al. | 5,849,859 A | 12/1998 | Acemoglu |
| 5,718,726 A | 2/1998 | Amon et al. | 5,851,508 A | 12/1998 | Greff et al. |
| 5,720,726 A | 2/1998 | Marcadis et al. | 5,853,408 A | 12/1998 | Muni |
| 5,721,131 A | 2/1998 | Rudolph et al. | 5,854,207 A | 12/1998 | Lee et al. |
| 5,722,984 A | 3/1998 | Fischell et al. | 5,854,376 A | 12/1998 | Higashi |
| 5,723,219 A | 3/1998 | Kolluri et al. | 5,855,598 A | 1/1999 | Pinchuk ................. 623/1 |
| 5,725,549 A | 3/1998 | Lam | 5,855,612 A | 1/1999 | Ohthuki et al. |
| 5,726,297 A | 3/1998 | Gryaznov et al. | 5,855,618 A | 1/1999 | Patnaik et al. |
| 5,728,068 A | 3/1998 | Leone et al. | 5,857,998 A | 1/1999 | Barry |
| 5,728,751 A | 3/1998 | Patnaik | 5,858,556 A | 1/1999 | Eckert et al. |
| 5,730,698 A | 3/1998 | Fischell et al. | 5,858,746 A | 1/1999 | Hubbell et al. |
| 5,733,326 A | 3/1998 | Tomonto et al. | 5,858,990 A | 1/1999 | Walsh |
| 5,733,327 A | 3/1998 | Igaki et al. | 5,860,954 A | 1/1999 | Ropiak |
| 5,733,330 A | 3/1998 | Cox | 5,865,814 A | 2/1999 | Tuch ..................... 604/265 |
| 5,733,564 A | 3/1998 | Lehtinen | 5,866,113 A | 2/1999 | Hendriks et al. |
| 5,733,925 A | 3/1998 | Kunz et al. | 5,868,781 A | 2/1999 | Killion |
| 5,735,897 A | 4/1998 | Buirge | 5,869,127 A | 2/1999 | Zhong |
| 5,741,554 A | 4/1998 | Tisone | 5,871,436 A | 2/1999 | Eury |
| 5,741,881 A | 4/1998 | Patnaik | 5,871,437 A | 2/1999 | Alt |
| 5,746,745 A | 5/1998 | Abele et al. | 5,873,904 A | 2/1999 | Ragheb et al. |
| 5,746,998 A | 5/1998 | Torchilin et al. | 5,874,101 A | 2/1999 | Zhong et al. |
| 5,756,457 A | 5/1998 | Wang et al. | 5,874,109 A | 2/1999 | Zhong et al. |
| 5,756,476 A | 5/1998 | Epstein et al. | 5,874,165 A | 2/1999 | Drumheller |
| 5,759,205 A | 6/1998 | Valentini | 5,874,355 A | 2/1999 | Huang et al. |
| 5,759,474 A | 6/1998 | Rupp et al. | 5,876,426 A | 3/1999 | Kume et al. |
| 5,765,682 A | 6/1998 | Bley et al. | 5,876,433 A | 3/1999 | Lunn |
| 5,766,204 A | 6/1998 | Porter et al. | 5,876,743 A | 3/1999 | Ibsen et al. |
| 5,766,239 A | 6/1998 | Cox | 5,877,224 A | 3/1999 | Brocchini et al. |
| 5,766,710 A | 6/1998 | Turnlund et al. | 5,877,263 A | 3/1999 | Patnaik et al. |
| 5,769,883 A | 6/1998 | Buscemi et al. | 5,879,713 A | 3/1999 | Roth et al. |
| 5,769,884 A | 6/1998 | Solovay | 5,883,011 A | 3/1999 | Lin et al. |
| 5,770,609 A | 6/1998 | Grainger et al. | 5,888,533 A | 3/1999 | Dunn |
| 5,772,864 A | 6/1998 | Møller et al. ................. 205/73 | 5,891,192 A | 4/1999 | Murayama et al. |
| 5,776,184 A | 7/1998 | Tuch | 5,893,840 A | 4/1999 | Hull et al. |
| 5,780,807 A | 7/1998 | Saunders | 5,893,852 A | 4/1999 | Morales |
| 5,782,742 A | 7/1998 | Crocker et al. | 5,895,407 A | 4/1999 | Jayaraman ................. 606/198 |
| 5,783,657 A | 7/1998 | Pavlin et al. | 5,897,911 A | 4/1999 | Loeffler ..................... 427/2.25 |
| 5,788,626 A | 8/1998 | Thompson ................... 600/36 | 5,897,955 A | 4/1999 | Drumheller |
| 5,788,979 A | 8/1998 | Alt et al. | 5,898,178 A | 4/1999 | Bunker |
| 5,800,392 A | 9/1998 | Racchini | 5,902,631 A | 5/1999 | Wang et al. |
| 5,800,516 A | 9/1998 | Fine et al. | 5,902,875 A | 5/1999 | Roby et al. |
| 5,804,318 A | 9/1998 | Pinchuk et al. | 5,905,168 A | 5/1999 | Dos Santos et al. |
| 5,807,244 A | 9/1998 | Barot | 5,906,759 A | 5/1999 | Richter |
| 5,810,871 A | 9/1998 | Tuckey et al. | 5,910,564 A | 6/1999 | Gruning et al. |
| 5,810,873 A | 9/1998 | Morales | 5,914,182 A | 6/1999 | Drumheller |
| 5,811,151 A | 9/1998 | Hendriks et al. | 5,914,387 A | 6/1999 | Roby et al. |
| 5,811,447 A | 9/1998 | Kunz et al. | 5,916,234 A | 6/1999 | Lam |
| 5,820,917 A | 10/1998 | Tuch ......................... 427/2.1 | 5,916,870 A | 6/1999 | Lee et al. |
| 5,823,996 A | 10/1998 | Sparks ........................ 604/96 | 5,919,893 A | 7/1999 | Roby et al. |
| 5,824,048 A | 10/1998 | Tuch | 5,921,416 A | 7/1999 | Uehara |
| 5,824,049 A | 10/1998 | Ragheb et al. | 5,922,005 A | 7/1999 | Richter et al. |
| 5,824,056 A | 10/1998 | Rosenberg | 5,922,393 A | 7/1999 | Jayaraman ................... 427/2.3 |
| 5,826,586 A | 10/1998 | Mishra et al. | 5,925,552 A | 7/1999 | Keogh et al. |
| 5,830,178 A | 11/1998 | Jones et al. | 5,925,720 A | 7/1999 | Kataoka et al. |
| 5,830,179 A | 11/1998 | Mikus et al. | 5,928,916 A | 7/1999 | Keogh |
| 5,830,217 A | 11/1998 | Ryan | 5,932,299 A | 8/1999 | Katoot |
| 5,830,461 A | 11/1998 | Billiar | 5,935,135 A | 8/1999 | Bramfitt et al. ............. 606/108 |
| 5,830,879 A | 11/1998 | Isner | 5,942,209 A | 8/1999 | Leavitt et al. |
| 5,833,644 A | 11/1998 | Zadno-Azizi et al. | 5,947,993 A | 9/1999 | Morales |
| 5,833,651 A | 11/1998 | Donovan et al. | 5,948,018 A | 9/1999 | Dereume et al. ............... 623/1 |
| 5,833,659 A | 11/1998 | Kranys ........................ 604/96 | 5,948,428 A | 9/1999 | Lee et al. |
| 5,834,582 A | 11/1998 | Sinclair et al. | 5,951,881 A | 9/1999 | Rogers et al. |
| 5,836,962 A | 11/1998 | Gianotti | 5,954,744 A | 9/1999 | Phan et al. |
| 5,836,965 A | 11/1998 | Jendersee et al. | 5,955,509 A | 9/1999 | Webber et al. |
| 5,837,008 A | 11/1998 | Berg et al. | 5,957,975 A | 9/1999 | Lafont et al. |
| 5,837,313 A | 11/1998 | Ding et al. | 5,958,385 A | 9/1999 | Tondeur et al. |

| | | | | | |
|---|---|---|---|---|---|
| 5,962,138 A | 10/1999 | Kolluri et al. | 6,110,188 A | 8/2000 | Narciso, Jr. |
| 5,965,720 A | 10/1999 | Gryaznov et al. | 6,110,483 A | 8/2000 | Whitbourne et al. |
| 5,968,091 A | 10/1999 | Pinchuk et al. | 6,113,629 A | 9/2000 | Ken |
| 5,968,092 A | 10/1999 | Buscemi et al. | 6,117,479 A | 9/2000 | Hogan et al. |
| 5,969,422 A | 10/1999 | Ting et al. | 6,117,979 A | 9/2000 | Hendricks et al. |
| 5,971,954 A | 10/1999 | Conway et al. | 6,120,477 A | 9/2000 | Campbell et al. |
| 5,972,027 A | 10/1999 | Johnson | 6,120,491 A | 9/2000 | Kohn et al. |
| 5,972,029 A | 10/1999 | Fuisz | 6,120,535 A | 9/2000 | McDonald et al. |
| 5,972,505 A | 10/1999 | Phillips et al. | 6,120,536 A | 9/2000 | Ding et al. |
| 5,976,155 A | 11/1999 | Foreman et al. | 6,120,788 A | 9/2000 | Barrows |
| 5,976,182 A | 11/1999 | Cox | 6,120,847 A | 9/2000 | Yang et al. .............. 427/335 |
| 5,980,564 A | 11/1999 | Stinson | 6,120,904 A | 9/2000 | Hostettler et al. |
| 5,980,928 A | 11/1999 | Terry | 6,121,027 A | 9/2000 | Clapper et al. |
| 5,980,972 A | 11/1999 | Ding | 6,123,712 A | 9/2000 | Di Caprio et al. |
| 5,981,568 A | 11/1999 | Kunz et al. | 6,125,523 A | 10/2000 | Brown et al. |
| 5,984,449 A | 11/1999 | Tajika et al. | 6,126,686 A | 10/2000 | Badylak et al. ............ 623/1.24 |
| 5,986,169 A | 11/1999 | Gjunter | 6,127,173 A | 10/2000 | Eckstein et al. |
| 5,997,468 A | 12/1999 | Wolff et al. | 6,129,761 A | 10/2000 | Hubbell |
| 5,997,517 A | 12/1999 | Whitbourne | 6,129,928 A | 10/2000 | Sarangapani et al. |
| 6,010,445 A | 1/2000 | Armini et al. | 6,132,809 A | 10/2000 | Hynes et al. |
| 6,010,530 A | 1/2000 | Goicoechea | 6,136,333 A | 10/2000 | Cohn et al. |
| 6,010,573 A | 1/2000 | Bowlin ................ 118/620 | 6,140,127 A | 10/2000 | Sprague |
| 6,011,125 A | 1/2000 | Lohmeijer et al. | 6,140,431 A | 10/2000 | Kinker et al. |
| 6,013,099 A | 1/2000 | Dinh et al. | 6,143,354 A | 11/2000 | Koulik et al. |
| 6,015,541 A | 1/2000 | Greff et al. | 6,143,370 A | 11/2000 | Panagiotou et al. |
| 6,019,789 A | 2/2000 | Dinh et al. | 6,149,574 A | 11/2000 | Trauthen et al. |
| 6,024,918 A | 2/2000 | Hendriks et al. | 6,150,630 A | 11/2000 | Perry et al. |
| 6,027,510 A | 2/2000 | Alt | 6,153,252 A | 11/2000 | Hossainy et al. ............ 427/2.3 |
| 6,027,526 A | 2/2000 | Limon et al. | 6,156,373 A | 12/2000 | Zhong et al. .............. 427/2.28 |
| 6,030,371 A | 2/2000 | Pursley | 6,159,227 A | 12/2000 | Di Caprio et al. |
| 6,033,582 A | 3/2000 | Lee et al. | 6,159,229 A | 12/2000 | Jendersee et al. |
| 6,033,719 A | 3/2000 | Keogh | 6,159,951 A | 12/2000 | Karpeisky et al. |
| 6,034,204 A | 3/2000 | Mohr et al. | 6,159,978 A | 12/2000 | Myers et al. |
| 6,042,606 A | 3/2000 | Frantzen | 6,160,084 A | 12/2000 | Langer et al. |
| 6,042,875 A | 3/2000 | Ding et al. | 6,165,212 A | 12/2000 | Dereume et al. |
| 6,045,899 A | 4/2000 | Wang et al. ............. 428/315.7 | 6,166,130 A | 12/2000 | Rhee et al. |
| 6,048,964 A | 4/2000 | Lee et al. | 6,168,617 B1 | 1/2001 | Blaeser et al. |
| 6,051,021 A | 4/2000 | Frid | 6,168,619 B1 | 1/2001 | Dinh et al. |
| 6,051,576 A | 4/2000 | Ashton et al. | 6,169,170 B1 | 1/2001 | Gryaznov et al. |
| 6,051,648 A | 4/2000 | Rhee et al. | 6,171,609 B1 | 1/2001 | Kunz |
| 6,054,553 A | 4/2000 | Groth et al. | 6,172,167 B1 | 1/2001 | Stapert et al. |
| 6,056,906 A | 5/2000 | Werneth et al. | 6,174,316 B1 | 1/2001 | Tuckey et al. |
| 6,056,993 A | 5/2000 | Leidner et al. ............ 427/2.25 | 6,174,330 B1 | 1/2001 | Stinson |
| 6,059,752 A | 5/2000 | Segal | 6,177,523 B1 | 1/2001 | Reich et al. |
| 6,059,810 A | 5/2000 | Brown et al. | 6,180,632 B1 | 1/2001 | Myers et al. |
| 6,060,451 A | 5/2000 | DiMaio et al. | 6,183,505 B1 | 2/2001 | Mohn, Jr. et al. |
| 6,060,518 A | 5/2000 | Kabanov et al. | 6,187,045 B1 | 2/2001 | Fehring et al. |
| 6,063,092 A | 5/2000 | Shin | 6,193,727 B1 | 2/2001 | Foreman et al. |
| 6,066,156 A | 5/2000 | Yan | 6,203,551 B1 | 3/2001 | Wu |
| 6,071,266 A | 6/2000 | Kelley | 6,209,621 B1 | 4/2001 | Treacy |
| 6,071,305 A | 6/2000 | Brown et al. | 6,210,715 B1 | 4/2001 | Starling et al. |
| 6,074,659 A | 6/2000 | Kunz et al. | 6,211,249 B1 | 4/2001 | Cohn et al. |
| 6,080,099 A | 6/2000 | Slater et al. | 6,214,115 B1 | 4/2001 | Taylor et al. ................ 118/423 |
| 6,080,177 A | 6/2000 | Igaki et al. | 6,214,407 B1 | 4/2001 | Laube et al. |
| 6,080,190 A | 6/2000 | Schwartz | 6,214,901 B1 | 4/2001 | Chudzik et al. |
| 6,080,488 A | 6/2000 | Hostettler et al. | 6,217,586 B1 | 4/2001 | Mackenzie |
| 6,083,258 A | 7/2000 | Yadav | 6,217,721 B1 | 4/2001 | Xu et al. |
| 6,086,610 A | 7/2000 | Duerig et al. | 6,224,626 B1 | 5/2001 | Steinke |
| 6,090,330 A | 7/2000 | Gawa et al. | 6,224,675 B1 | 5/2001 | Prentice et al. |
| 6,093,199 A | 7/2000 | Brown et al. | 6,224,894 B1 | 5/2001 | Jamiolkowski et al. |
| 6,093,463 A | 7/2000 | Thakrar | 6,228,845 B1 | 5/2001 | Donovan et al. |
| 6,096,070 A | 8/2000 | Ragheb et al. | 6,231,590 B1 | 5/2001 | Slaikeu et al. |
| 6,096,525 A | 8/2000 | Patnaik | 6,231,600 B1 | 5/2001 | Zhong |
| 6,099,455 A | 8/2000 | Columbo et al. | 6,240,616 B1 | 6/2001 | Yan |
| 6,099,559 A | 8/2000 | Nolting | 6,242,041 B1 | 6/2001 | Katoot et al. |
| 6,099,561 A | 8/2000 | Alt | 6,245,076 B1 | 6/2001 | Yan |
| 6,099,562 A | 8/2000 | Ding et al. | 6,245,099 B1 | 6/2001 | Edwin et al. ............... 623/1.13 |
| 6,103,230 A | 8/2000 | Billiar et al. | 6,245,103 B1 | 6/2001 | Stinson |
| 6,106,454 A | 8/2000 | Berg et al. | 6,245,753 B1 | 6/2001 | Byun et al. |
| 6,106,530 A | 8/2000 | Harada | 6,245,760 B1 | 6/2001 | He et al. |
| 6,106,889 A | 8/2000 | Beavers et al. | 6,248,129 B1 | 6/2001 | Froix |
| 6,107,416 A | 8/2000 | Patnaik et al. | 6,248,344 B1 | 6/2001 | Ylanen et al. |
| 6,110,180 A | 8/2000 | Foreman et al. | 6,251,135 B1 | 6/2001 | Stinson et al. |

| Patent | Date | Inventor(s) |
|---|---|---|
| 6,251,136 B1 | 6/2001 | Guruwaiya et al. |
| 6,251,142 B1 | 6/2001 | Bernacca et al. |
| 6,253,443 B1 | 7/2001 | Johnson |
| 6,254,632 B1 | 7/2001 | Wu et al. |
| 6,258,099 B1 | 7/2001 | Mareiro et al. |
| 6,258,121 B1 | 7/2001 | Yang et al. ................ 623/1.46 |
| 6,258,371 B1 | 7/2001 | Koulik et al. |
| 6,262,034 B1 | 7/2001 | Mathiowitz et al. |
| 6,270,504 B1* | 8/2001 | Lorentzen Cornelius et al. .......................... 606/108 |
| 6,270,788 B1 | 8/2001 | Koulik et al. |
| 6,273,850 B1 | 8/2001 | Gambale et al. |
| 6,273,913 B1 | 8/2001 | Wright et al. |
| 6,277,110 B1 | 8/2001 | Morales |
| 6,277,449 B1 | 8/2001 | Kolluri et al. |
| 6,279,368 B1 | 8/2001 | Escano et al. ............. 72/342.1 |
| 6,281,262 B1 | 8/2001 | Shikinami |
| 6,283,947 B1 | 9/2001 | Mirzaee |
| 6,283,949 B1 | 9/2001 | Roorda |
| 6,284,305 B1 | 9/2001 | Ding et al. |
| 6,284,333 B1 | 9/2001 | Wang et al. |
| 6,287,332 B1 | 9/2001 | Bolz et al. |
| 6,287,628 B1 | 9/2001 | Hossainy et al. |
| 6,290,721 B1 | 9/2001 | Heath |
| 6,293,966 B1 | 9/2001 | Frantzen |
| 6,294,836 B1 | 9/2001 | Paranjpe et al. |
| 6,296,603 B1 | 10/2001 | Turnlund et al. |
| 6,299,604 B1 | 10/2001 | Ragheb et al. |
| 6,303,901 B1 | 10/2001 | Perry et al. |
| 6,306,176 B1 | 10/2001 | Whitbourne |
| 6,312,459 B1 | 11/2001 | Huang et al. |
| 6,319,520 B1 | 11/2001 | Wuthrich et al. |
| 6,322,588 B1 | 11/2001 | Ogle et al. |
| 6,322,847 B1 | 11/2001 | Zhong et al. ............... 427/2.28 |
| 6,327,772 B1 | 12/2001 | Zadno-Azizi et al. |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,362,099 B1 | 3/2002 | Gandikota et al. |
| 6,364,903 B2 | 4/2002 | Tseng et al. ................ 623/1.15 |
| 6,375,458 B1 | 4/2002 | Moorleghem et al. |
| 6,375,826 B1 | 4/2002 | Wang et al. |
| 6,379,379 B1 | 4/2002 | Wang |
| 6,379,381 B1 | 4/2002 | Hossainy et al. |
| 6,387,118 B1 | 5/2002 | Hanson ..................... 623/1.11 |
| 6,387,121 B1 | 5/2002 | Alt |
| 6,387,379 B1 | 5/2002 | Goldberg et al. |
| 6,388,043 B1 | 5/2002 | Langer et al. |
| 6,395,325 B1 | 5/2002 | Hedge et al. |
| 6,395,326 B1 | 5/2002 | Castro et al. |
| 6,406,738 B1 | 6/2002 | Hogan et al. |
| 6,409,761 B1 | 6/2002 | Jang |
| 6,413,272 B1 | 7/2002 | Igaki |
| 6,419,692 B1 | 7/2002 | Yang et al. |
| 6,420,189 B1 | 7/2002 | Lopatin |
| 6,423,092 B2 | 7/2002 | Datta et al. |
| 6,436,816 B1 | 8/2002 | Lee et al. |
| 6,444,567 B1 | 9/2002 | Besser et al. |
| 6,447,835 B1 | 9/2002 | Wang et al. |
| 6,451,373 B1 | 9/2002 | Hossainy et al. |
| 6,454,738 B1 | 9/2002 | Tran et al. |
| 6,455,424 B1 | 9/2002 | McTeer et al. |
| 6,461,632 B1 | 10/2002 | Gogolewski |
| 6,462,284 B1 | 10/2002 | Hashimoto |
| 6,464,720 B2 | 10/2002 | Boatman et al. |
| 6,468,906 B1 | 10/2002 | Chan et al. |
| 6,479,565 B1 | 11/2002 | Stanley |
| 6,481,262 B2 | 11/2002 | Ching et al. |
| 6,482,834 B2 | 11/2002 | Spada et al. |
| 6,485,512 B1 | 11/2002 | Cheng |
| 6,488,701 B1 | 12/2002 | Nolting et al. |
| 6,488,773 B1 | 12/2002 | Ehrhardt et al. |
| 6,491,666 B1 | 12/2002 | Santini, Jr. et al. |
| 6,492,615 B1 | 12/2002 | Flanagan |
| 6,494,862 B1 | 12/2002 | Ray et al. |
| 6,494,908 B1 | 12/2002 | Huxel et al. |
| 6,495,156 B2 | 12/2002 | Wenz et al. |
| 6,495,200 B1 | 12/2002 | Chan et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,504,307 B1 | 1/2003 | Malik et al. |
| 6,506,437 B1 | 1/2003 | Harish et al. |
| 6,510,722 B1 | 1/2003 | Ching et al. |
| 6,511,748 B1 | 1/2003 | Barrows |
| 6,517,888 B1 | 2/2003 | Weber |
| 6,517,889 B1 | 2/2003 | Jayaraman |
| 6,521,284 B1 | 2/2003 | Parsons et al. ............. 427/2.24 |
| 6,524,232 B1 | 2/2003 | Tang et al. |
| 6,524,347 B1 | 2/2003 | Myers et al. |
| 6,527,801 B1 | 3/2003 | Dutta |
| 6,527,863 B1 | 3/2003 | Pacetti et al. ................ 118/500 |
| 6,528,526 B1 | 3/2003 | Myers et al. |
| 6,530,950 B1 | 3/2003 | Alvarado et al. |
| 6,530,951 B1 | 3/2003 | Bates et al. |
| 6,537,589 B1 | 3/2003 | Chae et al. |
| 6,539,607 B1 | 4/2003 | Fehring et al. |
| 6,540,776 B2 | 4/2003 | Sanders Millare et al. |
| 6,540,777 B2 | 4/2003 | Stenzel |
| 6,544,223 B1 | 4/2003 | Kokish |
| 6,544,543 B1 | 4/2003 | Mandrusov et al. |
| 6,544,582 B1 | 4/2003 | Yoe |
| 6,554,758 B2 | 4/2003 | Turnlund et al. |
| 6,554,854 B1 | 4/2003 | Flanagan |
| 6,555,059 B1 | 4/2003 | Myrick et al. |
| 6,555,157 B1 | 4/2003 | Hossainy |
| 6,558,733 B1 | 5/2003 | Hossainy et al. |
| 6,562,136 B1 | 5/2003 | Chappa et al. |
| 6,565,599 B1 | 5/2003 | Hong et al. |
| 6,565,659 B1 | 5/2003 | Pacetti et al. ................ 118/500 |
| 6,569,191 B1 | 5/2003 | Hogan |
| 6,569,193 B1 | 5/2003 | Cox et al. |
| 6,572,644 B1 | 6/2003 | Moein ........................ 623/1.11 |
| 6,572,672 B2 | 6/2003 | Yadav et al. |
| 6,574,851 B1 | 6/2003 | Mirizzi |
| 6,575,933 B1* | 6/2003 | Wittenberger et al. .. 604/101.02 |
| 6,582,417 B1 | 6/2003 | Ledesma et al. |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,592,614 B2 | 7/2003 | Lenker et al. |
| 6,592,617 B2 | 7/2003 | Thompson |
| 6,596,296 B1 | 7/2003 | Nelson et al. |
| 6,605,114 B1 | 8/2003 | Yan et al. |
| 6,605,154 B1 | 8/2003 | Villareal ..................... 118/500 |
| 6,605,874 B2 | 8/2003 | Leu et al. |
| 6,610,087 B1 | 8/2003 | Zarbatany et al. |
| 6,613,072 B2 | 9/2003 | Lau et al. |
| 6,616,765 B1 | 9/2003 | Wu et al. |
| 6,623,448 B2 | 9/2003 | Slater |
| 6,625,486 B2 | 9/2003 | Lundkvist et al. |
| 6,626,939 B1 | 9/2003 | Burnside et al. |
| 6,635,269 B1 | 10/2003 | Jennissen |
| 6,635,964 B2 | 10/2003 | Maex et al. |
| 6,645,135 B1 | 11/2003 | Bhat |
| 6,645,195 B1 | 11/2003 | Bhat et al. |
| 6,645,243 B2 | 11/2003 | Vallana et al. |
| 6,645,547 B1 | 11/2003 | Shekalim et al. |
| 6,656,162 B2 | 12/2003 | Santini, Jr. et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |

| | | | | | | |
|---|---|---|---|---|---|---|
| 6,664,187 B1 | 12/2003 | Ngo et al. | | 2002/0077693 A1 | 6/2002 | Barclay et al. |
| 6,664,335 B2 | 12/2003 | Krishnan | | 2002/0082679 A1 | 6/2002 | Sirhan et al. |
| 6,666,214 B2 | 12/2003 | Canham | | 2002/0087123 A1 | 7/2002 | Hossainy et al. |
| 6,666,880 B1 | 12/2003 | Chiu et al. | | 2002/0091433 A1 | 7/2002 | Ding et al. |
| 6,667,049 B2 | 12/2003 | Janas et al. | | 2002/0094440 A1 | 7/2002 | Llanos et al. |
| 6,669,723 B2 | 12/2003 | Killion et al. | | 2002/0111590 A1 | 8/2002 | Davila et al. |
| 6,669,980 B2 | 12/2003 | Hansen | | 2002/0116050 A1 | 8/2002 | Kocur |
| 6,673,385 B1 | 1/2004 | Ding et al. | | 2002/0120326 A1 | 8/2002 | Michal |
| 6,676,697 B1 | 1/2004 | Richter | | 2002/0138133 A1 | 9/2002 | Lenz et al. |
| 6,676,700 B1 | 1/2004 | Jacobs et al. | | 2002/0142039 A1 | 10/2002 | Claude |
| 6,679,980 B1 | 1/2004 | Andreacchi | | 2002/0155212 A1 | 10/2002 | Hossainy |
| 6,689,099 B2 | 2/2004 | Mirzaee | | 2002/0161114 A1 | 10/2002 | Gunatillake et al. |
| 6,689,375 B1 | 2/2004 | Wahlig et al. | | 2002/0165608 A1 | 11/2002 | Llanos et al. |
| 6,703,307 B2 | 3/2004 | Lopatin et al. | | 2002/0176849 A1 | 11/2002 | Slepian |
| 6,706,013 B1 | 3/2004 | Bhat et al. | | 2002/0183581 A1 | 12/2002 | Yoe et al. |
| 6,706,273 B1 | 3/2004 | Roessler | | 2002/0187632 A1 | 12/2002 | Marsh |
| 6,709,379 B1 | 3/2004 | Brandau et al. | | 2002/0188037 A1 | 12/2002 | Chudzik et al. |
| 6,709,514 B1 | 3/2004 | Hossainy | | 2002/0188277 A1 | 12/2002 | Roorda et al. |
| 6,712,845 B2 | 3/2004 | Hossainy | | 2003/0003221 A1 | 1/2003 | Zhong et al. |
| 6,713,119 B2 | 3/2004 | Hossainy et al. | | 2003/0004141 A1 | 1/2003 | Brown |
| 6,716,444 B1 | 4/2004 | Castro et al. | | 2003/0028243 A1 | 2/2003 | Bates et al. |
| 6,719,934 B2 | 4/2004 | Stinson | | 2003/0028244 A1 | 2/2003 | Bates et al. |
| 6,719,989 B1 | 4/2004 | Matsushima et al. | | 2003/0031780 A1 | 2/2003 | Chudzik et al. |
| 6,720,402 B2 | 4/2004 | Langer et al. | | 2003/0032767 A1 | 2/2003 | Tada et al. |
| 6,723,120 B2 | 4/2004 | Yan | | 2003/0033001 A1 | 2/2003 | Igaki |
| 6,733,768 B2 | 5/2004 | Hossainy et al. | | 2003/0036794 A1 | 2/2003 | Ragheb et al. |
| 6,740,040 B1 | 5/2004 | Mandrusov et al. | | 2003/0039689 A1 | 2/2003 | Chen et al. |
| 6,743,462 B1 | 6/2004 | Pacetti | | 2003/0040712 A1 | 2/2003 | Ray et al. |
| 6,746,773 B2 | 6/2004 | Llanos et al. | | 2003/0040790 A1 | 2/2003 | Furst |
| 6,749,626 B1 | 6/2004 | Bhat et al. | | 2003/0054090 A1 | 3/2003 | Hansen |
| 6,752,826 B2 | 6/2004 | Holloway et al. | | 2003/0055482 A1 | 3/2003 | Schwager et al. |
| 6,753,007 B2 | 6/2004 | Haggard et al. | | 2003/0059520 A1 | 3/2003 | Chen et al. |
| 6,753,071 B1 | 6/2004 | Pacetti | | 2003/0060877 A1 | 3/2003 | Falotico et al. |
| 6,758,859 B1 | 7/2004 | Dang et al. | | 2003/0065377 A1 | 4/2003 | Davila et al. |
| 6,759,054 B2 | 7/2004 | Chen et al. | | 2003/0072868 A1 | 4/2003 | Harish et al. |
| 6,764,505 B1 | 7/2004 | Hossainy et al. | | 2003/0073961 A1 | 4/2003 | Happp |
| 6,774,278 B1 | 8/2004 | Ragheb et al. | | 2003/0083646 A1 | 5/2003 | Sirhan et al. |
| 6,776,792 B1 | 8/2004 | Yan et al. | | 2003/0083739 A1 | 5/2003 | Cafferata |
| 6,783,793 B1 | 8/2004 | Hossainy et al. | | 2003/0088307 A1 | 5/2003 | Shulze et al. |
| 6,846,323 B2 | 1/2005 | Yip et al. | | 2003/0093107 A1 | 5/2003 | Parsonage et al. |
| 6,860,946 B2 | 3/2005 | Hossainy et al. | | 2003/0097088 A1 | 5/2003 | Pacetti |
| 6,861,088 B2 | 3/2005 | Weber et al. | | 2003/0097173 A1 | 5/2003 | Dutta |
| 6,865,810 B2 | 3/2005 | Stinson | | 2003/0099712 A1 | 5/2003 | Jayaraman |
| 6,869,443 B2 | 3/2005 | Buscemi et al. | | 2003/0100865 A1 | 5/2003 | Santini, Jr. et al. |
| 6,878,160 B2 | 4/2005 | Gilligan et al. | | 2003/0105518 A1 | 6/2003 | Dutta |
| 6,887,270 B2 | 5/2005 | Miller et al. | | 2003/0105530 A1 | 6/2003 | Pirhonen |
| 6,887,485 B2 | 5/2005 | Fitzhugh et al. | | 2003/0113439 A1 | 6/2003 | Pacetti et al. |
| 6,890,546 B2 | 5/2005 | Mollison et al. | | 2003/0113445 A1 | 6/2003 | Martin |
| 6,899,731 B2 | 5/2005 | Li et al. | | 2003/0138487 A1 | 7/2003 | Hogan et al. |
| 7,011,675 B2 * | 3/2006 | Hemerick et al. ......... 623/1.12 | | 2003/0150380 A1 | 8/2003 | Yoe |
| 2001/0007083 A1 | 7/2001 | Roorda | | 2003/0157241 A1 | 8/2003 | Hossainy et al. |
| 2001/0014717 A1 | 8/2001 | Hossainy et al. | | 2003/0158517 A1 | 8/2003 | Kokish |
| 2001/0016753 A1 | 8/2001 | Caprio et al. | | 2003/0171053 A1 | 9/2003 | Sanders |
| 2001/0020011 A1 | 9/2001 | Mathiowitz et al. | | 2003/0185964 A1 | 10/2003 | Weber et al. |
| 2001/0029351 A1 | 10/2001 | Falotico et al. | | 2003/0187495 A1 | 10/2003 | Cully et al. |
| 2001/0037145 A1 | 11/2001 | Guruwaiya et al. | | 2003/0190406 A1 | 10/2003 | Hossainy et al. |
| 2001/0044652 A1 | 11/2001 | Moore | | 2003/0203617 A1 | 10/2003 | Lane et al. |
| 2001/0051608 A1 | 12/2001 | Mathiowitz et al. | | 2003/0207020 A1 | 11/2003 | Villareal |
| 2002/0002399 A1 | 1/2002 | Huxel et al. | | 2003/0208259 A1 | 11/2003 | Penhasi |
| 2002/0004060 A1 | 1/2002 | Heublein et al. | | 2003/0209835 A1 | 11/2003 | Chun et al. |
| 2002/0004101 A1 | 1/2002 | Ding et al. | | 2003/0211230 A1 | 11/2003 | Pacetti et al. |
| 2002/0005206 A1 | 1/2002 | Falotico et al. | | 2003/0226833 A1 | 12/2003 | Shapovalov et al. |
| 2002/0007213 A1 | 1/2002 | Falotico et al. | | 2003/0236565 A1 | 12/2003 | DiMatteo et al. |
| 2002/0007214 A1 | 1/2002 | Falotico | | 2004/0018296 A1 | 1/2004 | Castro et al. |
| 2002/0007215 A1 | 1/2002 | Falotico et al. | | 2004/0029952 A1 | 2/2004 | Chen et al. |
| 2002/0009604 A1 | 1/2002 | Zamora et al. | | 2004/0047978 A1 | 3/2004 | Hossainy et al. |
| 2002/0016625 A1 | 2/2002 | Faltico et al. | | 2004/0047980 A1 | 3/2004 | Pacetti et al. |
| 2002/0032414 A1 | 3/2002 | Ragheb et al. | | 2004/0052858 A1 | 3/2004 | Wu et al. |
| 2002/0032434 A1 | 3/2002 | Chudzik et al. | | 2004/0052859 A1 | 3/2004 | Wu et al. |
| 2002/0051730 A1 | 5/2002 | Bodnar et al. | | 2004/0054104 A1 | 3/2004 | Pacetti |
| 2002/0062148 A1 | 5/2002 | Hart | | 2004/0060508 A1 | 4/2004 | Pacetti et al. |
| 2002/0065553 A1 | 5/2002 | Weber | | 2004/0063805 A1 | 4/2004 | Pacetti et al. |
| 2002/0071822 A1 | 6/2002 | Uhrich | | 2004/0072922 A1 | 4/2004 | Hossainy et al. |

| | | | | | | |
|---|---|---|---|---|---|---|
| 2004/0086542 | A1 | 5/2004 | Hossainy et al. | EP | 0 974 315 | 1/2000 |
| 2004/0093077 | A1 | 5/2004 | White et al. | EP | 0 982 041 | 3/2000 |
| 2004/0098117 | A1 | 5/2004 | Hossainy et al. | EP | 1 023 879 | 8/2000 |
| 2004/0111149 | A1 | 6/2004 | Stinson | EP | 1 034 752 | 9/2000 |
| 2004/0127970 | A1 | 7/2004 | Saunders | EP | 1 075 838 | 2/2001 |
| 2004/0143317 | A1 | 7/2004 | Stinson et al. | EP | 1 103 234 | 5/2001 |
| 2004/0167610 | A1 | 8/2004 | Fleming, III. | EP | 1 192 957 | 4/2002 |
| 2004/0213893 | A1 | 10/2004 | Boulais | EP | 1 273 314 | 1/2003 |
| 2005/0038497 | A1 | 2/2005 | Neuendorf et al. | EP | 0 869 847 | 3/2003 |
| 2005/0043786 | A1 | 2/2005 | Chu et al. | FR | 2 753 907 | 4/1998 |
| 2005/0049694 | A1 | 3/2005 | Neary | GB | 2 247 696 | 3/1992 |
| 2005/0054774 | A1 | 3/2005 | Kangas | GB | 2 316 086 | 1/2000 |
| 2005/0055044 | A1 | 3/2005 | Kangas | GB | 2 316 342 | 1/2000 |
| 2005/0060020 | A1 | 3/2005 | Jenson | GB | 2 333 975 | 1/2000 |
| 2005/0064088 | A1 | 3/2005 | Fredrickson | GB | 2 336 551 | 1/2000 |
| 2005/0065501 | A1 | 3/2005 | Wallace | GB | 2 356 586 | 5/2001 |
| 2005/0065545 | A1 | 3/2005 | Wallace | GB | 2 356 587 | 5/2001 |
| 2005/0065593 | A1 | 3/2005 | Chu et al. | GB | 2 333 474 | 6/2001 |
| 2005/0074545 | A1 | 4/2005 | Thomas | GB | 2 334 685 | 6/2001 |

FOREIGN PATENT DOCUMENTS

| | | | | | |
|---|---|---|---|---|---|
| GB | 2 356 585 | 7/2001 |
| GB | 2 374 302 | 8/2001 |
| CA | 2 007 648 | 4/1991 | GB | 2 370 243 | 6/2002 |
| CA | 1 322 628 | 10/1993 | GB | 2 384 199 | 7/2003 |
| CA | 1 336 319 | 7/1995 | JP | SHO49-48336 | 12/1974 |
| CA | 1 338 303 | 5/1996 | JP | SHO54-18310 | 7/1979 |
| DE | 042 24 401 | 1/1994 | JP | SHO60-28504 | 7/1985 |
| DE | 044 07 079 | 9/1994 | JP | 21199867 | 5/1994 |
| DE | 197 31 021 | 1/1999 | JP | HEI8-33718 | 2/1996 |
| DE | 199 16 086 | 10/1999 | JP | HEI10-151190 | 6/1998 |
| DE | 198 56 983 | 12/1999 | JP | 2919971 B2 | 7/1999 |
| EP | 0 108 171 | 5/1984 | JP | 2001-190687 | 7/2001 |
| EP | 0 144 534 | 6/1985 | SU | 0872531 | 10/1981 |
| EP | 0 301 856 | 2/1989 | SU | 0876663 | 10/1981 |
| EP | 0 380 668 | 4/1989 | SU | 0905228 | 2/1982 |
| EP | 0 351 314 | 1/1990 | SU | 0790725 | 2/1983 |
| EP | 0 364 787 | 4/1990 | SU | 1016314 | 5/1983 |
| EP | 0 396 429 | 11/1990 | SU | 0811750 | 9/1983 |
| EP | 0 397 500 | 11/1990 | SU | 1293518 | 2/1987 |
| EP | 0 464 755 | 1/1992 | SU | 1477423 | 5/1989 |
| EP | 0 493 788 | 7/1992 | WO | WO 89/03232 | 4/1989 |
| EP | 0 526 606 | 9/1992 | WO | WO 90/01969 | 3/1990 |
| EP | 0 514 406 | 11/1992 | WO | WO 90/04982 | 5/1990 |
| EP | 0 517 075 | 12/1992 | WO | WO 90/06094 | 6/1990 |
| EP | 0 540 290 | 5/1993 | WO | WO 91/11176 | 8/1991 |
| EP | 0 553 960 | 8/1993 | WO | WO 91/12846 | 9/1991 |
| EP | 0 554 082 | 8/1993 | WO | WO 91/17744 | 11/1991 |
| EP | 0 565 251 | 10/1993 | WO | WO 91/17789 | 11/1991 |
| EP | 0 578 998 | 1/1994 | WO | WO 92/10218 | 6/1992 |
| EP | 0 604 022 | 6/1994 | WO | WO 93/06792 | 4/1993 |
| EP | 0 621 017 | 10/1994 | WO | WO 94/09760 | 5/1994 |
| EP | 0 623 354 | 11/1994 | WO | WO 94/21196 | 9/1994 |
| EP | 0 627 226 | 12/1994 | WO | WO 95/10989 | 4/1995 |
| EP | 0 649 637 | 4/1995 | WO | WO 95/11817 | 5/1995 |
| EP | 0 665 023 | 8/1995 | WO | WO 95/24929 | 9/1995 |
| EP | 0 701 802 | 3/1996 | WO | WO 95/29647 | 11/1995 |
| EP | 0 701 803 | 3/1996 | WO | WO 95/33422 | 12/1995 |
| EP | 0 709 068 | 5/1996 | WO | WO 96/28115 | 9/1996 |
| EP | 0 716 836 | 6/1996 | WO | WO 96/35516 | 11/1996 |
| EP | 0 732 087 | 9/1996 | WO | WO 96/40174 | 12/1996 |
| EP | 0 832 618 | 9/1996 | WO | WP 97/10011 | 3/1997 |
| EP | 0 756 853 | 2/1997 | WO | WO 97/45105 | 12/1997 |
| EP | 0 809 999 | 12/1997 | WO | WO 97/46590 | 12/1997 |
| EP | 0 832 655 | 4/1998 | WO | WO 98/04415 | 2/1998 |
| EP | 0 834 293 | 4/1998 | WO | WO 98/07390 | 2/1998 |
| EP | 0 850 604 | 7/1998 | WO | WO 98/08463 | 3/1998 |
| EP | 0 850 651 | 7/1998 | WO | WO 98/17331 | 4/1998 |
| EP | 0 879 595 | 11/1998 | WO | WO 98/20863 | 5/1998 |
| EP | 0 910 584 | 4/1999 | WO | WO 98/23228 | 6/1998 |
| EP | 0 923 953 | 6/1999 | WO | WO 98/32398 | 7/1998 |
| EP | 0 953 320 | 11/1999 | WO | WO 98/36784 | 8/1998 |
| EP | 0 970 711 | 1/2000 | WO | WO 99/01118 | 1/1999 |
| EP | 0 972 498 | 1/2000 | WO | WO 99/03515 | 1/1999 |
| | | | WO | WO 99/16386 | 4/1999 |

| | | |
|---|---|---|
| WO | WO 99/38546 | 8/1999 |
| WO | WO 99/42147 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17459 | 3/2001 |
| WO | WO 01/17577 | 3/2001 |
| WO | WO 01/43721 | 6/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/57144 | 8/2001 |
| WO | WO 01/74414 | 10/2001 |
| WO | WO 01/91918 | 12/2001 |
| WO | WO 02/03890 | 1/2002 |
| WO | WO 02/026162 | 4/2002 |
| WO | WO 02/034311 | 5/2002 |
| WO | WO 02/047731 | 6/2002 |
| WO | WO 02/049771 | 6/2002 |
| WO | WO 02/056790 | 7/2002 |
| WO | WO 02/058753 | 8/2002 |
| WO | WO 02/087550 | 8/2002 |
| WO | WO 02/102283 | 12/2002 |
| WO | WO 03/000308 | 1/2003 |
| WO | WO 03/007918 | 1/2003 |
| WO | WO 03/007919 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/061841 | 7/2003 |
| WO | WO 03/072084 | 9/2003 |
| WO | WO 03/072086 | 9/2003 |

OTHER PUBLICATIONS

Anonymous, *Capillary Action*, http://www.ndt-ed.org/EducationResources/CommunityCollege/PenetrantTest/Introduction/Keywords/pt1.htm, printed Aug. 12, 2005, 1 page.

Anonymous, *Capillary Force Lithography (CFL)*, Nano Processing and Organic Devices Lab, 2 pages, no date.

Anonymous, *Capillary Rise of Liquid in Different Vanes Under Variable Residual Accleration*, http://www.zarm.uni-bremen.de/2forschung/grenzph/isoterm/cap_rise/kapst_en.htm, ZARM—University of Bremen, printed Jun. 25, 2003, 2 pages.

Anonymous, *Cardiologists Draw—Up The Dream Stent*, Clinica 710, pp. 15 (Jun. 17, 1996), http://www.dialogweb.com/cgi/document?reg=1061848202958, printed Aug. 25, 2003, 2 pages.

Anonymous, *Coating Techniques, Air Knife Coating*, http://www.ferron-magnetic.co.uk/coatings/airknife.htm, printed Jul. 1, 2003, 1 page.

Anonymous, *Coating Techniques, Gap Coating (Knife Over Roll, etc.)*, http://www.ferron-magnetic.co.uk/coatings/knife.htm, printed Jul. 1, 2003, 1 page.

Anonymous, *Coating Techniques, Gravure Coating*, http://www.ferron-magnetic.co.uk/coatings/gravure.htm, printed Jul. 1, 2003, 2 pages.

Anonymous, *Coating Techniques, Reverse Roll Coating*, http://www.ferron-magnetic.co.uk/coatings/revroll.html, printed Jul. 1, 2003, 22 pages.

Anonymous, *Heparin-coated stents cut complications By 30%*, Clinica 732, pp. 17 (Nov. 18, 1996), http://www.dialogweb.com/cgi/document?reg=1061847871753, printed Aug. 25, 2003, 2 pages.

Anonymous, *Liquid Gravity Motor*, http://www.drspark86.com/idea001.html, printed Jun. 24, 2003, 2 pages, no date.

Anonymous, *Porosimetry—Why characterize the porosity?* 42 pages, no date.

Anonymous, *Stenting Continues to Dominate Cardiology*, http://www.dialogweb.com/cgi/document?reg=1061848017752, Clinica vol. 720, pp. 22 (Sep. 2, 1996), printed Aug. 25, 2003, 2 pages.

Anonymous, *Surface Energy (Surface Wetting Capability)*, http://www.ndt-ed.org/EducationResources/CommunityCollege/PenetrantTest/PTMaterials/surfacenergy.htm, printed Apr. 6, 2004, 3 pages, no date.

Anonymous, *The 14th International Young Physicists Tournament, The winning report*, Research Center for Quantum Information, Slovak Academy of Sciences, 5 pages, no date.

Anonymous, *The Wicking Wall System*, http://www.decorative.com/wicking.html, printed Jun. 24, 2003, 1 page.

Anonymous, *Typical Parylene Properties*, 3 pages, no date.

Anonymous, *Viscosity*, Commonwealth of Australia, 7 pages, no date.

Ansari, *End-to-End Tubal Anastomosis Using an Absorbable Stent*, Fertility and Sterility, vol. 32, No. 2, pp. 197-201 (Aug. 1979).

Ansari, *Tubal Reanastomosis Using Absorbable Stent*, International Journal of Fertility, vol. 23, No. 4, pp. 242-243 (1978).

Aoyagi et al., *Preparation of cross-linked aliphatic polyester and application to thermo-responsive material*, Journal of Controlled Release 32, pp. 87-96 (1994).

Barath et al., *Low Dose of Antitumor Agents Prevents Smooth Muscle Cell Proliferation After Endothelial Injury*, JACC vol. 3, No. 2, pp. 252A (Feb. 1989).

Barbucci et al., *Coating of Commercially available materials with a new heparinizable Material*, Journal of Biomedical Materials Research, vol. 25, pp. 1259-1274 (1991).

Beach et al., *Xylylene Polymers*, Encyclopedia of Polymer Science and Engineering, vol. 17, 2nd Edition, pp. 990-1025 (1989).

Boston Scientific, *Express²™ Coronary Stent System*, http://www.bostonscientific.com/med_specialty/deviceDetail.jsp?task=tskBasicDevice.jsp&sectionId=4&relId=2,74,75,76&deviceId=11001&unique=MPDB1180&clickType=endeca, printed Aug. 8, 2005, 1 page.

Bull, *Parylene Coating for Medical Applications*, Medical Product Manufacturing News, 2 pages (Mar. 1993).

Casper et al., *Fiber-Reinforced Absorbable Composite for Orthopedic Surgery*, Polymeric Materials Science and Engineering, vol. 53, pp. 497-501 (1985).

Charlson et al., *Temperature Selective Deposition of Parylene-C*, IEEE Transactions of Biomedical Engineering, vol. 39, No. 2, pp. 202-206 (Feb. 1992).

Chen et al., *The Kinetics of Wicking of Liquid Droplets into Yams*, submitted to the Textile Research Journal, pp. 1-30 (Apr. 2001).

Chung et al. *Inner core segment design for drug delivery control of thermo-responsive polymeric micelles*, Journal of Controlled Release, vol. 65, pp. 93-103 (2000).

Crowe et al., *Absorption and Intestinal Metabolism of SDZ-RAD and Rapamycin in Rats*, Drug Metabolism and Disposition, vol. 27, No. 5, pp. 627-632 (1999).

De Scheerder et al., *Bicompatibility of polymer-coated oversized metallic stents implanted in normal porcine coronary arteries* Atherosclerosis, vol. 114, pp. 105-114 (1995).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9, No. 2, pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis* Journal of Investigative Surgery, vol. 9, No. 6, pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8, No. 2, pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9, No. 1, pp. 13-26 (Jan./Feb. 1996).

Dev et al., *Kinetics of Drug Delivery to the Arterial Wall Via Polyurethane-Coated Removable Nitinol Stent: Comparative Study of Two Drugs*, Catheterization and Cardiovascular Diagnosis, vol. 34, pp. 272-278 (1995).

Devanathan et al., *Polymeric Conformal Coatings for Implantable Electronic Devices*, IEEE Transactions on Biomedical Engineering, vol. BME-27, No. 11, pp. 671-675 (1980).

Dichek et al., *Seeding of Intravascular Stents with Genetically Engineered Endothelial Cells*, Circulation, vol. 80, No. 5, pp. 1347-1353 (Nov. 1989).

Dreyer et al., *Critical Velocities in Open Capillary Flows*, pp. 604-609, no date.

Duerig et al., *A comparison of balloon-and self-expanding stents*, Min. Invas. Ther. & Allied Technol., vol. 11, No. 4, pp. 173-178 (2002).

Dutkiewicz, *Some Advances in Nonwoven Structures for Absorbency, Comfort and Aesthetics*, AUTEX Research Journal, vol. 2, No. 3, pp. 153-165 (Sep. 2002).

EFD, *780S Series Spray Valves VALVEMATE™ 7040 Controller Operating Manual*, 24 pages (2002).

Eigler et al., *Local Arterial Wall Drug Delivery from a Polymer Coated Removable Metallic Stent: Kinetics, Distribution, and Bioactivity of Forskolin*, JACC, vol. 4A, pp. 701-701, Abstract (Feb. 1994).

Elbert et al., *Conjugate Addition Reactions Combined with Free-Radical Cross-Linking for the Design of Materials for Tissue Engineering*, Biomacromolecules, vol. 2, pp. 430-441 (2001).

Erickson et al., *Numerical Simulations of Capillary-Driven Flows in Nonuniform Cross-Sectional Capillaries*, Journal of Colloid and Interface Science, vol. 250, pp. 422-430 (2002).

Eskin et al., *Growth of Cultured Calf Aortic Smooth Muscle Cells on Cardiovascular Prosthetic Materials*, J. Biomed. Mater. Res. vol. 10, pp. 113-122 (1976).

Eskin et al., *Tissue Cultured Cells: Potential Blood Compatible Linings for Cardiovascular Prostheses*, Polymer Science and Technology, vol. 14, pp. 143-161, no date.

Fischell et al., *Low-Dose, β-Particle Emission from 'Stent' Wire Results in Complete, Localized Inhibition of Smooth Muscle Cell Proliferation*, Circulation, vol. 90, No. 6, pp. 2956-2963 (Dec. 1994).

Fischell et al., *The Bx VELOCITY™ STENT*, 5 pages, Biocompatibles Ltd. (2001).

Gengenbach et al., *Evolution of the Surface Composition and Topography of Perflurinated Polymers Following Ammonia-Plasma Treatment*, Plasma Surface Modifications of Polymers, pp. 123-146 (1994).

Gercken et al., *Results of the Jostent Coronary Stent Graft Implantation in Various Clinical Settings: Procedural and Follow-Up Results*, vol.56, No. 3, pp. 353-360 (2002).

Gölander et al., *RF-Plasma-Modified Polystyrene Surfaces for Studying Complement Activation*, J. Biomater. Sci. Plmer Edn., vol. 4, No. 1, pp. 25-30 (1992).

Guidant, *ACS RX Multi-Link™ Coronary Stent System*, 6 pages, no date.

Guidant, *Guidant Multi-Link Vision OTW Coronary Stent System*, 2 pages, no date.

Hahn et al., *Biocompatibility of Glow-Discharge-Polymerized Films and Vacuum-Deposited Parylene*, Journal of Applied Polymer Science: Applied Polymer Symposium 38, 55-64 (1984).

Hahn et al., *Glow Discharge Polymers as Coatings for Implanted Devices*, John M. Dalton Research Center, University of Missouri-Columbia and the Graduate Center for Materials Research, pp. 109-113 (1981).

He et al., *Assessment of Tissue Blood Flow Following Small Artery Welding with an Intraluminal Dissolvable Stent*, Microsurgery, vol. 19, No. 3, pp. 148-152 (1999).

Hehrlein et al., *Low-Dose Radioactive Endovascular Stetns Prevent Smooth Muscle Cell Proliferation and Neointimal Hyperplasia in Rabbits*, Circulation, vol. 92, No. 6, pp. 1570-1575 (Sep. 15, 1995).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol., vol. 3, pp. 197-199 (1998).

Hollahan et al., *Attachment of Amino Groups to Polymer Surfaces by Radiofrequency Plasmas*, Journal of Applied Polymer Science, vol. 13, pp. 807-816 (1969).

Huang et al., *Biodegradable Polymers Derived from Aminoacides*, Marcomol. Symp. 144, 7-32 (1999).

Impulse Jetting, *About Us*, http://www.impulsejetting.com/about.html, printed Dec. 18, 2000, 1 page.

Impulse Jetting, *Our Technology*, http://www.impulsejetting.com/tech1.html, printed Dec. 18, 2000, 1 page.

Inagaki et al., *Hydrophilic Surface Modification of Polyethylene by No-Plasma Treatment*, Adhesion Sci. Technol., vol. 4, No. 2, pp. 99-107 (1990).

Inoue et al., *An AB block copolymer of oligo(methyl methacrylate) and poly(acrylic acid) for micellar delivery of hydrophobic drugs*, Journal of Controlled Release, vol. 51, pp. 221-229 (1998).

Itabashi et al., *Electroless Deposited CoWB for Copper Diffusion Barrier Metal*, International Interconnect Technology Conference, pp. 285-287 (2002).

John Ritchie Production Group, *Production of Stents* (presentation), 15 pages (Apr. 24, 2003).

Kataoka et al., *Block Copolymer Micelles as Vehicles for Drug Delivery*, Journal of Controlled Release vol. 24, pp. 119-132 (1993).

Katsarava et al., *Amino Acid-Based Bioanalogous Polymers. Synthesis and Study of Regular Poly(ester amide)s Based on Bis(α-amino acid) α,ω-Alkylene Diesters, and Aliphatic Dicarbolic Acids*, Journal of Polymer Science, Part A: Polymer Chemistry, vol. 37, 391-407 (1999).

Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).

Kelley et al., *Totally Resorbable High-Strength Composite Material*, Advances in Biomedical Polymers, vol. 35, pp. 75-85 (1987).

Klocke et al, *How Soil Holds Water* (G90-964), http://ianrpubs.unl.edu/fieldcrops/g964.htm, printed Apr. 6, 2004, 9 pages.

Konopka, *In-Plane Moisture Transport in Nonwovens*, Nonwovens Cooperative Research Center, NC State University, 56 pages, no date.

Kovarik et al., *Pharmacokinetic and Pharmacodynamic Assessments of HMG-CoA Reductase Inhibitors When Coadminstered with Everolimus*, Journal of Clinical Pharmacology, vol. 42, pp. 222-228 (2002).

Kubies et al., *Microdomain Structure In polyactide-block-poly(ethylene oxide) copolymer films*, Biomaterials, vol. 21, pp. 529-536 (2000).

Kutryk et al., *Coronary Stenting: Current Perspectives, a companion to the Handbook of Coronary Stents*, 16 pages (1999).

Lambert et al., *Localized Arterial Wall Drug Delivery From a Polymer-Coated Removable Metallic Stent*, Circulation, vol. 90, No. 2, pp. 1003-1011 (Aug. 1994).

Lemos et al., *Coronary Restenosis After Sirolimus-Eluting Stent Implantation*, Circulation, vol. 108, No. 3, pp. 257-260 (Jul. 22, 2003).

Levy et al., *Strategies For Treating Arterial Restenosis Using Polymeric Controlled Release Implants*, Biotechnology and Bioactive Polymers, pp. 259-268 (1994).

Liu et al., *Drug Release Characteristics of Unimolecular Polymeric Micelles*, Journal of Controlled Release, vol. 68, pp. 167-174 (2000).

Loeb et al., *Parylene as a Chronically Stable, Reproducible Microelectrode Insulator*, IEEE Transactions on Biomedical Engineering, pp. 121-128 (Mar. 1977).

Loh et al., *Plasma Enhanced Parylene Deposition*, Antec, pp. 1099-1103 (1991).

Machine Solutions, *FFS700 MSI Balloon Form/Fold/Set Equipment (PTCA), FFS800 MSI Balloon Form/Fold/Set Equipment (PTA)*, http://machinesolutions.org/ffs7_8.html, printed Nov. 21, 2003 (2 pgs.).

Machine Solutions, *SC700 MSI Stent Crimping Equipment (PTCA), SC800 MSI Stent Crimping Equipment (PTA)*, http://www.machinesolutions.org/sc7_8.html, printed Nov. 21, 2003, 2 pages.

Malik et al., *Development of an Energetic Ion Assisted Mixing and Deposition Process for $Tin_x$ and Diamondlike Carbon Films, Using* a Co-axial Geometry in Plasma Source Ion Implantation, J. Vac. Sci. Technol. A, vol. 15, No. 6, pp. 2875-2879 (Nov./Dec. 1997).
Malik et al., Overview of plasma source ion implantation research at University of Wisconsin-Madison, J. Vac. Sci. Technol. B, No. 12, vol. 2, pp. 843-849 (Mar./Apr. 1994).
Malik et al., Sheath dynamics and dose analysis for planar targets in plasma source ion implantation, Plasma Sources Sci. Technol. vol. 2, pp. 81-85 (1993).
Marconi et al., Covalent bonding of heparin to a vinyl copolymer for biomedical applications, Biomaterials, vol. 18, No. 12, pp. 885-890 (1997).
Matsumaru et al., Embolic Materials For Endovascular Treatment of Cerebral Lesions, J. Biomater. Sci. Polymer Edn., vol. 8, No. 7, pp. 555-569 (1997).
Mauduit et al., Hydrolytic degradation of films prepared from blends of high and low molecular weight poly(DL-lactic acid)s, J. Biomed. Mater. Res., vol. 30, pp. 201-207 (1996).
Middleton et al., Synthetic biodegradable polymers as orthopedic devices, Biomaterials, vol. 21, pp. 2335-2346 (2000).
Miyazaki et al., Antitumor Effect of Implanted Ethylene-Vinyl Alcohol Copolymer Matrices Containing Anticancer Agents on Ehrlich Ascites Carcinoma and P388 Leukemia in Mice, Chem. Pharm. Bull., vol. 33, No. 6, pp. 2490-2498 (1985).
Miyazawa et al., Effects of Pemirolast and Tranilast on Intimal Thickening After Arterial Injury in the Rat, J. Cardiovas. Pharmacol., vol. 30, No. 2, pp. 157-162 (1997).
Moody, Vacuum Coating Ultrasonic Transducers, 1 page, Sensors (Dec. 1993).
Muller et al., Advances in Coronary Angioplasty: Endovascular Stents, Coronary Artery Disease, vol. 1, No. 4., pp. 438-448 (Jul./Aug. 1990).
Neimark et al., Hierarchical Pore Structure and Wetting Properties of Single-Wall Carbon Nanotube Fibers, Nano Letters, vol. 3, No. 3, pp. 419-423 (2003).
Nichols et al., Electrical Insulation of Implantable Devices by Composites Polymer Coatings, ISA Transactions, vol. 26, No. 4, pp. 15-18 (1987).
Nordrehaug et al., A Novel Biocompatible Coating Applied to Coronary Stents, EPO Heart Journal 14, p. 321 (P1694), Abstr. Suppl. (1993).
Nova Tran™ Custom Coating Services, Parylene Conformal Coating, 8 pages, no date.
Ohsawa et al., Preventive Effects of an Antiallergic Drug, Pemirolast Potassium, on Restenosis After Percutaneous Transluminal Coronary Angioplasty, American Heart Journal, vol. 136, No. 6, pp. 1081-1087 (Dec. 1998).
Olson, Parylene, a Biostabel Coating for Medical Applications, Speciality Coating Systems, Inc. Nova Tran™ Parylene Coating Services, no date.
Ozaki et al., New Stent Technologies, Progress in Cardiovascular Diseases, vol. XXXIX, No. 2, pp. 129-140 (Sep./Oct. 1996).
Para Tech Coating Company, Galxyl, Parylene Coatings by Para Tech, 1 page, no date.
Para Tech Coating Company, Lab Top® Parylene Deposition System, 2 pages, no date.
Pechar et al., Poly(ethylene glycol)Multiblock Copolymer as a Carrier of Anti-Cancer Drug Doxorubicin, Bioconjucate Chemistry vol. 11, No. 2, pp. 131-139 (Mar./ Apr. 2000).
Peng et al., Role of polymers in improving the results of stenting in coronary arteries, Biomaterial, vol. 17, pp. 685-694 (1996).
Peuster et al., A novel approach to temporary stenting: degradable cardiovascular stents produced from corrodible metal-results 6-18 months after implantation into New Zeland white rabbits, Heart vol. 86, pp. 563-569 (2001).
Pietrzak et al., Bioabsorbable Fixation Devices: Status for the Craniomaxillofacial Surgeon, Journal of Craniofacial Surgery, vol. 8, No. 2, pp. 92-96 (1997).
Pietrzak et al., Bioresorbable Implants—Practical Considerations, Bone, vol. 19, No. 1, Supplement, pp. 109S-119S (Jul. 1996).
Poncin-Epaillard et al., Reactivity of a Polypropylene Surface Modified in a Nitrogen Plasma, Plasma Surface Modification of Polymers pp. 167-180 (1994).

Redman, Clinical Experience with Vasovasostomy Utilizing Absorbable Intravasal Stent, Urology, vol. XX, No. 11, pp. 59-61 (Jul. 1982).
Refracton Technologies, Corp., Fine Bubble Diffusers, 2 pages (do date).
Refracton Technologies, Corp., Refractron Advanced Porous Ceramic Product Capabilities, http://www.refractron.com/ecom/sp/cat=Product+Information, printed Apr. 6, 2004, 3 pages.
Refracton Technologies Corp., http://www.refractron.com/ecom/sp/cat=Custom+Applications, printed Jun. 24, 2003, 1 page.
Rust et al., The Effect of Absorbable Stenting on Postoperative Stenosis of the Surgically Enlarged Maxillary Sinus Ostia in a Rabbit Animal Model, Archives of Otolaryngology, Head and Neck Surgery, vol. 122, pp. 1395-1397 (Dec. 1996).
Sadhir et al., The Adhesion of Glow-Discharge Polymers, Silastic And Parylene to Implantable Platinum Electrodes: Results of Tensil Pull tests After Exposure to Isotonic Sodium Chloride, Biomaterials, vol. 2, pp. 239-243 (Oct. 1981).
Saotome, et al., Novel Enzymatically Degradable Polymers Comprising α-Amino Acid, 1,2-Ethanediol, and Adipic Acid, Chemistry Letters, pp. 21-24, (1991).
Schatz, A View of Vascular Stents, Circulation, vol. 79, No. 2, pp. 445-457 (Feb. 1989).
Scheuer et al., Model of plasma source ion implantation in planar, cylindrical, and spherical geometries, J. Appl. Phys., vol. 67, No. 3, pp. 1241-1245 (Feb. 1990).
Schmidt et al., Long-term Implants of Parylene-C Coated Microelectrodes, Medical & Biological Engineering & Computing, pp. 96-101 (Jan. 1988).
Serkova et al., Tissue Distribution and Clinical Monitoring of the Novel Macrolide Immunosuppresant SDZ-RAD and its Metabolites in Monkey Lung Transplant Recipients: Interaction with Cyclosporine, The Journal of Pharmacology and Experimental Therapeutics, vol. 294, No. 1, pp. 323-332 (2000).
Serruys et al., I Like the Candy, I Hate the Wrapper; the $^{32}P$ Radioactive Stent, Circulation, vol. 101, pp. 3-7 (Jan. 2000).
Shamim et al., Measurement of electron emission due to energetic ion bombardment in plasma source ion implantation, J. Appl. Phys., vol. 70, No. 9, pp. 4756-4759 (Nov. 1991).
Shamim et al., Measurements of Spatial and Temporal Sheath Evolution for Spherical and Cylindrical Geometries in Plasma Source Ion Implantation, J. Appl. Phys., vol. 69, No. 5, pp. 2904-2908 (Mar. 1991).
Shigeno, Prevention of Cerebrovascular Spasm By Bosentan, Novel Endothelin Receptor; Chemical Abstract 125:21230 (1996).
Sono Tek Corporation, AccuMist™ for Single Stent Coating Applications, http://www.sono-tek.com/biomedical/accumist_stent.html, printed Aug. 2, 2005, 3 pages.
Sono Tek Corporation, MediCoat™ DES 1000, Benchtop Stent Coating System, http://www.sono-tek.com/biomedical/medicoat_standalone.html, printed Aug. 2, 2005, 4 pages.
Sono Tek Corporation, MicroMist for Stent Coating, http://www.sono-tek.com/biomedical/micromist_stent.html, printed Aug. 2, 2005, 3 pages.
Specialty Coating Systems, Inc., The Parylene Press, 4 pages (Summer 1993).
Specialty Coating Systems, Inc., The Parylene Press, 6 pages (Spring 1993).
Specialty Coating Systems, Inc., The Parylene Press, 7 pages, (Winter 1992).
Specialty Coating Systems, Parylene and Nova Tran™ Parylene Coating Services, for Unmatched Conformal Coating Performance, 21 pages, no date.
Specialty Coating Systems, Parylene, a Biostable Coating for Medical Applications, 6 pages, no date.
Specialty Coating Systems, Repair and Recoating of Parylene Coated Printed Circuit Boards, 15 pages, no date.
Straube, Moisture, Materials, & Buildings, HPAC Engineering, pp. 2-7, no date.
Taher, Capillary interaction between a small thin solid plate and a liquid, Mechanical and Industrial Engineering, University of Illinois at Urbana-Champaign, 4 pages, no date.

Tamai et al., *Initial and 6-Month Results of Biodegradable Poly-I-Lactic Acid Coronary Stents in Humans*, Circulation, vol. 102, pp. 399-404 (2000).
Trident, Inc., http://www.tridentintl.com/subbody.html, printed Dec. 18, 2000, 1 page.
Trident, Inc., *Product Lines*, http://www.tridentintl.com/products-apps/ultrajet.html, printed Dec. 18, 2000, 3 pages.
Tsuji et al., *Biodegradable Polymeric Stents*, Current Interventional Cardiology Reports vol. 3, pp. 10-17 (2001).
Union Carbide Adhesion Promoters, *Union Carbide A-174 Silane*, 5 pages (Jan. 1968).
Union Carbide Electronics Division, *Parylene Environmentally Compatible Conformal Coatings for Electronic Components Assemblies and Precision Parts*, 14 pages, no date.
Union Carbide, *Abrasion Resistance of Parylene and Other Conformal Circuit Board Coatings*, Parylene Products, No. 4, 13 pages (Oct. 1977).
Union Carbide, *Adhesion Promotion Systems for Parylene*, Parylene Products, No. 15, Revision 1, 8 pages (Oct. 1977).
Union Carbide, *Adhesion Promotion Systems for Parylene*, Technology Letter, No. 15, 13 pages (Oct. 1975).
Union Carbide, *Evaluation of Parylene and Other Pellicles as Beam Splitters*, Parylene Products, No. 8, Edited, 19 pages (Oct. 1977).
Union Carbide, *Fluorescent Parylene Coatings*, Parylene Products, No. 7, Revision 1, 8 pages (Oct. 1977).
Union Carbide, *Fluorescent Parylene Coatings*, Technology Letter, No. 7, 8 pages (Oct. 1973).
Union Carbide, *Mechanical Protection Criteria for Thin Conformal Coatings*, Parylene Products, No. 3, 21 pages (Oct. 1977).
Union Carbide, *Method for Repair and Patching of Parylene Coated Printed Circuit Boards*, Parylene Products, No. 2, Revision 1, 9 pages (Oct. 1977).
Union Carbide, *Microencapsulation by Vapor Deposition*, Parylene Products, No. 6, 12 pages (Oct. 1977).
Union Carbide, *MIL I 46058, Qualification of Parylene N, C, and D*, Parylene Products, No. 1, Revision 2, 8 pages (Oct. 1977).
Union Carbide, *Parylene Bibliography*, Parylene Products, No. 5, Revision 4, 17 pages (Jan. 18, 1982).
Union Carbide, *Parylene Conformal Coatings for Hybrid Microelectronics*, Parylene Products, No. 9, 23 pages (Oct. 1973).
Union Carbide, *Parylene Pellicles for Space Applications*, Parylene Products, No. 10, 50 pages (Oct. 1977).
Union Carbide, *Parylene Pyrolysis Kinetics*, Parylene Products, No. 11, 12 pages (Oct. 1977).
Union Carbide, *Parylene Pyrolysis Kinetics*, Technology Letter, No. 11, 12 pages (May 1974).
Union Carbide, *Parylene Removal with Oxygen Plasmas*, Parylene Products, No. 18, 7 pages (Aug. 1977).
Union Carbide, *Printed Circuit Board Masking Techniques for Use with Parylene*, No. 14, Revision 1, 11 pages (Oct. 1977).
Union Carbide, *Solvent Resistance of the Parylenes*, Parylene Products, No. 12, Revision 1, 5 pages (Oct. 1977).
Union Carbide, *The Selective Removal of Parylene by Plasma Etching*, No. 13, Revision 1, 7 pages (Oct. 1977).
Union Carbide, *Thermal Endurance of the Parylenes in Air*, Parylene Products, No. 16, 4 pages (Mar. 1976).
Union Carbide, *Vapor Phase Adhesion Promotion Systems*, Parylene Products, No. 17, Revision 1, 11 pages (Oct. 1977).
van Beusekom et al., *Coronary Stent Coatings*, Coronary Artery Disease, vol. 5, No. 7, pp. 590-596 (Jul. 1994).
van der Giessen et al., *"Edge Effect" of $^{32}$ P Radioactive Stents is Caused by the Combination of Chronic Stent Injury and Radioactive Dose Falloff*, Circulation, vol. 104, pp. 2236-2241 (Oct. 30, 2001).
Vapor Inc., *Vapore-Jet™ Capillary Pump—How it Works*, http://www.vapore.com/tech_howto.html, printed Aug. 13, 2003, 2 pages.
von Recum et al., *Degradation of polydispersed poly(L-lactic acid) to modulate lactic acid release*, Biomaterials, vol. 16, pp. 441-445 (1995).
Wiesendanger et al., *Contributions of Scanning Probe Microscopy and Spectroscopy to the Investigation and Fabrication of Nanometer-Scale Structures*, J. Vac. Sci. Technol. B, vol. 12, No. 2, pp. 515-529 (Mar./Apr. 1994).
Willensky et al., *Methods and Devices for Local Drug Delivery in Coronary and Peripheral Arteries*, Trends Cardiovasc. Med., vol. 3, No. 5, pp. 163-170 (1993).
Wong et al., *An Update on Coronary Stents*, Cardio, 8 pages (Feb. 1992).
World Precision Instruments, Inc., http://www.wpiinc.com/WPI_Web/Pumps/pneumatic_Fig.gif, printed Sep. 30, 2002, 1 page.
World Precision Instruments, Inc., *Nanoliter Injector*, http://www.wpiinc.com/WPI_Web/Microinjection/Nanoliter_Injector.html, printed Jun. 10, 2005, 3 pages.
World Precision Instruments, Inc., *Nanoliter Injector*, http://www.wpi-europe.com/products/microinjection/nanoliter.htm printed Jun. 10, 2005, 2 pages.
World Precision Instruments, Inc., *Pneumatic PicoPumps*, http://www.wpieurope.com/products/microinjection/picopumps.htm, printed Jun. 10, 2005, 4 pages.
World Precision Instruments, Inc., *Pneumatic PicoPumps*, http://www.wpiinc.com/WPI_Web/Microinjection/Pneumatic_PicoPumps.html, printed Jun. 10, 2005, 4 pages.
Yau et al., *Modern Size-Exclusion Liquid Chromatography*, Wiley-Interscience Publication, 9 pages (1979).
Yokoyama et al., *Characterization of physical entrapment and chemical conjugation of adriamycin in polymeric micelles and their design for in vivo delivery to asolid tumor*, Journal of Controlled Release, vol. 50, pp. 79-92 (1998).
Yuen et al., *Tissue response to potential neuroprosthetic materials implanted subdurally*, Biomaterials, vol. 8, pp. 57-62 (Mar. 1987).
Zhmud et al., *Dynamics of Capillary Rise*, Journal of Colloid and Interface Science, vol. 228, pp. 263-269 (2000).
Zimarino et al., *Analysis of Stent Edge Restenosis with Different Forms of Brachytherapy*, The American Journal of Cardiology, vol. 89, pp. 322-325 (Feb. 1, 2002).
Zylberman et al., *Comparative Study of Electroless Co(W,P) and Co(Mo,P) Thin-Films for Capping and Barrier Layers for Cu Metallization*, 2002 Advanced Metallization Conference, 2 pages, no date.

* cited by examiner

Unexpanded

Expanded

Unexpanded

Expanded

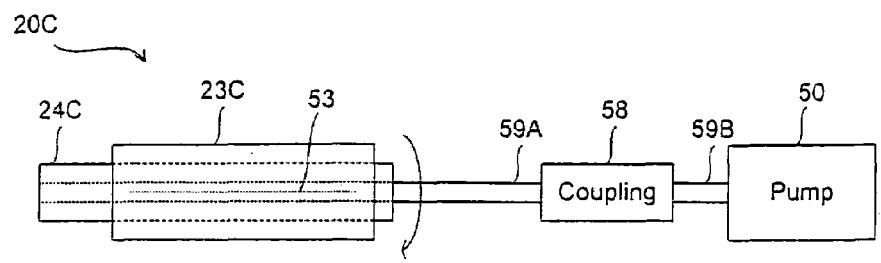
FIG. 3D
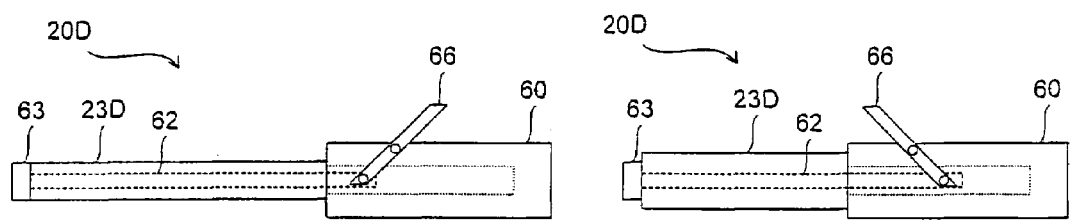
Unexpanded
FIG. 4A
Expanded
FIG. 4B
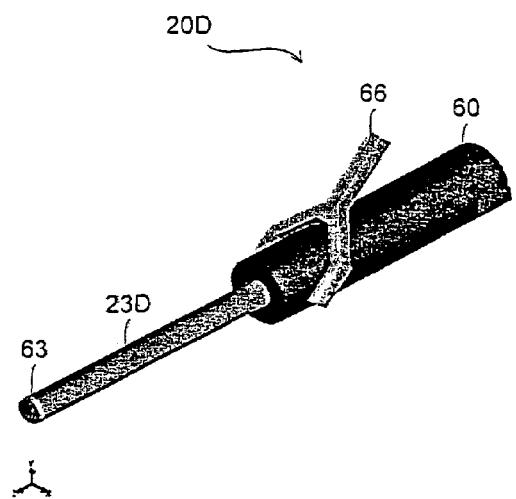
FIG. 4C Unexpanded Expanded

STENT MANDREL FIXTURE AND METHOD FOR SELECTIVELY COATING SURFACES OF A STENT

TECHNICAL FIELD

This invention relates generally to stent mandrel fixtures, and more particularly, but not exclusively, provides a stent mandrel fixture and method for coating an outer surface of a stent.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. The struts 12 and the connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is that both the inner surface and an outer surface of the stent are coated with the same therapeutic substance. Accordingly, the therapeutic substance will be dispensed locally by being absorbed by the vessel wall from the outer surface of the stent and will be dispensed downstream as blood carries the therapeutic substance from the inner surface. In some circumstances there may be a need of only having the outer surface of the stent coated with the therapeutic substance. Alternatively, there may be a need of coating the outer surface of the stent with a first type of a drug and the inner surface with a second type of a drug. For example, the stent's outer surface could be coated with an anti-inflamatory drug or anti-restenosis drug to treat inflammation or hyper-migration and proliferation of vascular smooth muscle cells, respectively. The stent's inner wall could be coating with an anti-coagulant to reduce platelet aggregation, clotting and thrombus formation.

Accordingly, a new stent mandrel fixture and method are needed to overcome this shortcoming.

SUMMARY

In accordance with one embodiment of the invention, a stent mandrel fixture is provided, comprising a masking element configured to be inserted through a bore of a stent, the masking element having an expanded configuration and a retracted configuration and an expansion causing mechanism capable of expanding the masking element from the retracted configuration to the expanded configuration to cause the masking element to make contact with and mask an inner surface of the stent.

In accordance with another embodiment of the invention, a fixture to support a stent during the application of a coating composition to the stent is provided, comprising a hollow tubular member configured to be inserted into a longitudinal bore of a stent; a rod extending through the tubular member; and a mechanism to cause the tubular member to expand and retract to support the stent during the application of a coating composition to the stent.

In accordance with another embodiment of the invention, a fixture to support a stent during the application of a coating composition to the stent is provided, comprising a mandrel base; a rod extending out from the mandrel base, the rod configured to be moved in and out of the mandrel base; and a support element integrated with the rod, the support element having a first position of being engaged with the stent and a second position of being disengaged from the stent, wherein the movement of the rod in and out of the mandrel base causes the engagement and disengagement of the support element with the stent. A lever can be used to drive the rod in and out of the mandrel base.

In accordance with other embodiments of the invention, methods of coating a stent with a composition are provided, comprising: positioning a stent on a fixture of the invention; and applying a coating composition to the stent.

In accordance with yet another embodiment, a method of coating a stent with a composition is provided, comprising inserting a tubular member inside a longitudinal bore of a stent, the stent comprising struts separated by gaps; expanding the tubular member such that the tubular member at least partially extends through the gaps; and applying a coating composition to the stent.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 3D illustrates a stent mandrel fixture in accordance with another embodiment of the invention;

FIG. 4A, FIG. 4B, FIG. 4C, and FIG. 4D illustrate a stent mandrel fixture in accordance with another embodiment of the invention;

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
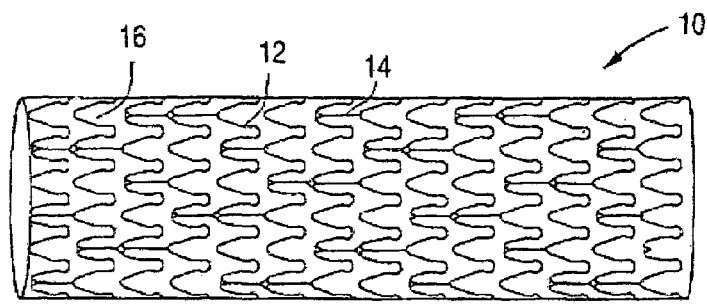
FIG. 1 illustrates a conventional stent.
Figure 2A:
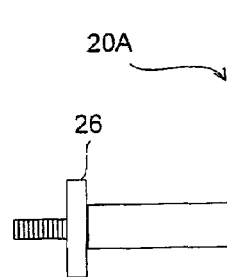
FIG. 2A and FIG. 2B illustrate a stent mandrel fixture in accordance with an embodiment of the invention.
Figure 2B:
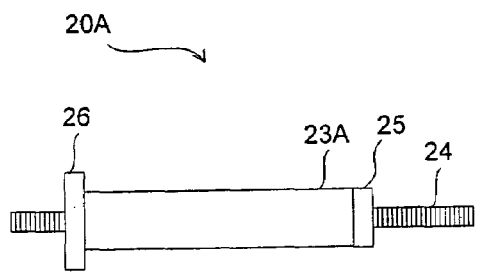

FIG. 2A and FIG. 2B illustrate a stent mandrel fixture 20A in accordance with an embodiment of the invention. The fixture 20A for supporting the stent 10 includes a bladder or expandable or elastic tube 23A, a threaded rod 24, a nut 25, and a lock member 26. The stent mandrel fixture 20A can be coupled to engines (not shown) to provide rotational and lateral motion to a mounted stent 10 during a coating process.

The threaded rod 24 passes through an inner bore of the tube 23A, lock member 26, and nut 25. The tube 23A is fixed at one end to the lock member 26 while the nut is rotationally mounted on the rod 24. In an alternative embodiment, the lock member 26 can also be rotationally mounted to the rod 24 (and therefore not fixed to the tube 23A) thereby enabling the adjustable positioning of the lock member 26. While the lock member 26 as shown has an outer diameter greater than the outer diameter of the nut 25, it will be appreciated by one of ordinary skill in the art that the lock member 26 can have an outer diameter less than, substantially equal to, or greater than the outer diameter of the nut 25. The outer diameter of the lock member 26 must only be at least equal to the outer diameter of the stent 10 so that the stent 10 does not slide past the lock member 26.

The nut 25 is an expansion causing mechanism. Rotation of the nut 25, such that the nut 25 presses against the tube 23A, causes the tube 23A to compress in a lateral direction against the lock member 26 while expanding radially outwards from the rod 24 as shown in FIG. 2B and FIG. 5B. Rotation of the nut 25 away from the tube 23A causes the tube 23A to return back to its uncompressed or natural state as shown in FIG. 2A and FIG. 5A.

It will be appreciated by one of ordinary skill in the art that the nut 25 can be electrically driven or otherwise tightened without human intervention in order to automate the process of coating a stent 10, thereby increasing throughput. Additionally, with the use of the nut 25, incremental rotation of the nut 25 can allow for the bladder or tube 23A to be expanded in an incremental fashion.

The tube 23A can be made of or coated with a non-stick substance, such as TEFLON. In one embodiment, the tube 23A, when compressed laterally, has a length equal to at least the length of the stent 10, thereby enabling masking of the entire length of the inner diameter of the stent 10. In another embodiment, the tube 23A, when compressed laterally, has a length shorter than the length of the stent 10, thereby supporting the stent 10 with minimal contact with the stent 10. In an unexpanded state (i.e., not compressed laterally), the tube 23A has an outer diameter smaller than the inner diameter of the stent 10 (as positioned on the tube 23A). When the tube 23A expands (i.e., is compressed laterally), the outer diameter of the tube 23A expands to at least the inner diameter of the stent 10, thereby acting to hold the stent 10 in place and to mask at least a portion of the inner surface of the stent 10. The masking of the inner surface of the stent 10 prevents the inner surface from being coated with a composition during a coating process. Accordingly, when the tube 23A is in an expanded state, only the outer surface and sidewalls of the stent 10 are coated with the composition from a spray flow, which is discharged from a nozzle assembly (not shown). In other embodiments of the invention to be discussed further below in conjunction with FIG. 6A to 6D, the tube 23A can be further radially expanded to enable masking of the sidewalls in addition to the inner surface of the stent 10.

Figure 5A:
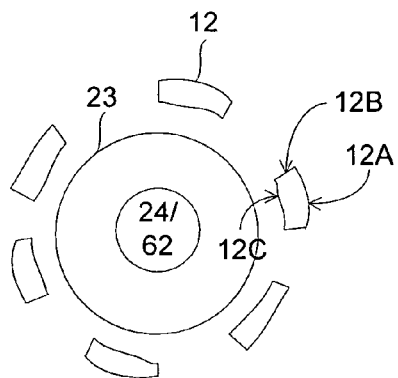
FIG. 5A and FIG. 5B illustrate cross sections of a stent mandrel fixture according to an embodiment of the invention.
Figure 5B:
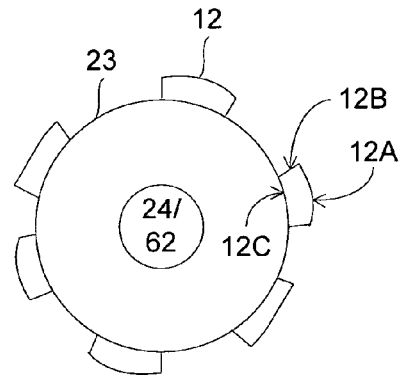
Figure 6A:
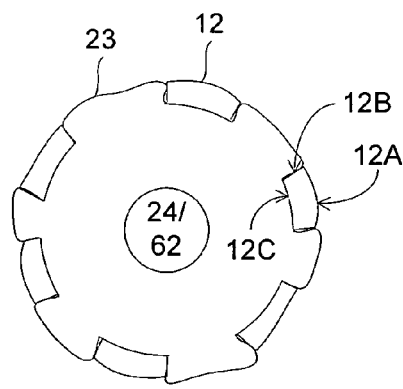
FIG. 6A illustrates a cross section of a stent mandrel fixture according to an embodiment of the invention.
Figure 6B:
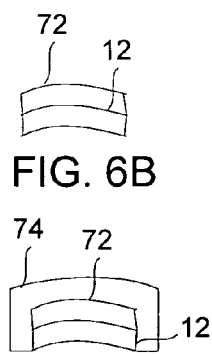
FIG. 6B–6D illustrate cross sections of a stent strut after coating on the stent mandrel fixture of FIG. 2, FIG. 3, or FIG. 4.
Figure 6C:
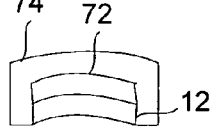
Figure 6D:
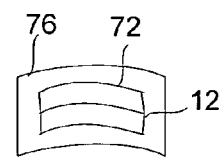

During operation of the stent mandrel fixture 20A, a stent 10 is loaded onto the fixture by first removing the nut 25 and then placing the stent 10 over the tube 23A when tube 23A is in an uncompressed state, as shown in FIG. 5A. The nut 25 is then loaded onto the rod 24 and tightened against the tube 23A, causing the tube 23A to compress laterally and expand radially outwards from the rod 24, as shown in FIG. 5B. In one embodiment of the invention, the tube 23A can expand radially outwards to substantially mask the inner surface of the stent 10, as shown in FIG. 5B. In another embodiment of the invention, the tube 23A can comprise a flexible and/or thin material, such as latex, and expands radially outwards to substantially mask the inner surface of the stent 10 as well as the sidewalls of the stent 10, as shown in FIG. 6A. In other words, the tube 23A is capable of protruding at least partially through the gaps 16 between the stent struts 12 to mask the sidewalls of the stent struts 12.

After the tube 23A is expanded radially outwards, a spray nozzle (not shown) sprays a composition onto the stent 10. As the inner diameter of the stent 10 is masked, only the sidewalls and outer surface of the stent 10 are coated with a composition. In another embodiment of the invention, the sidewalls can also be masked and accordingly, only the outer surface of the stent 10 is coated with the composition.

After the coating of the stent 10, the nut 25 is loosened, thereby enabling the tube 23A to return to a non-expanded state and further enabling removal of the stent 10 from the stent mandrel fixture 20A. The stent 10 can then have the inner surface coated via electroplating or spray coating. Without masking the outer surface of the stent 10, both electroplating and spray coating may yield some composition onto the outer surface and sidewalls of the stent 10. However, the inner surface would be substantially solely coated with a single composition different from the composition used to coat the outer surface of the stent 10. Accordingly, it will be appreciated by one of ordinary skill in the art that this embodiment enables the coating of the inner surface and the outer surface of the stent 10 with different compositions. For example, the inner surface could be coated with a composition having a bio-beneficial therapeutic substance for delivery downstream of the stent 10 (e.g., an anticoagulant, such as heparin, to reduce platelet aggregation, clotting and thrombus formation) while the outer surface of the stent 10 could be coating with a composition having a therapeutic substance for local delivery to a blood vessel wall (e.g., an anti-inflammatory drug to treat vessel wall inflammation or a drug for the treatment of restenosis).

The components of the coating substance or composition can include a solvent or a solvent system comprising multiple solvents, a polymer or a combination of polymers, a therapeutic substance or a drug or a combination of drugs. Representative examples of polymers that can be used to coat a stent or medical device include ethylene vinyl alcohol copolymer (commonly known by the generic name EVOH or by the trade name EVAL); poly(hydroxyvalerate); poly (L-lactic acid); polycaprolactone; poly(lactide-co-glycolide); poly(glycerol-sebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly (iminocarbonate); copoly(ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can include any substance capable of exerting a therapeutic or prophylactic effect. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$ actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

Figure 3A:
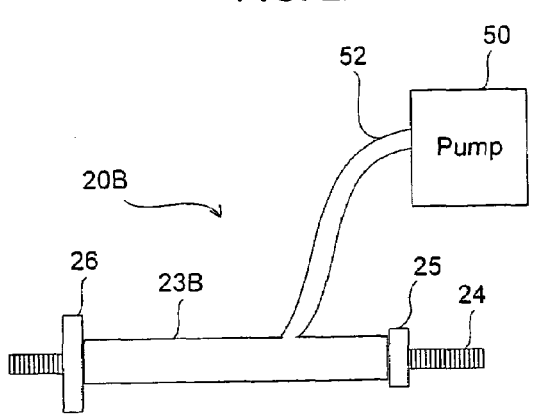
FIG. 3A, FIG. 3B, and FIG. 3C illustrate a stent mandrel fixture in accordance with another embodiment of the invention.
Figure 3B:
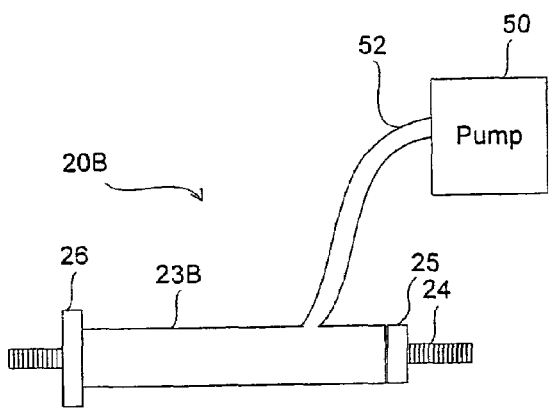
Figure 3C:
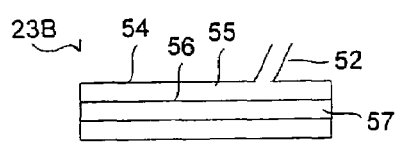
Figure 4D:
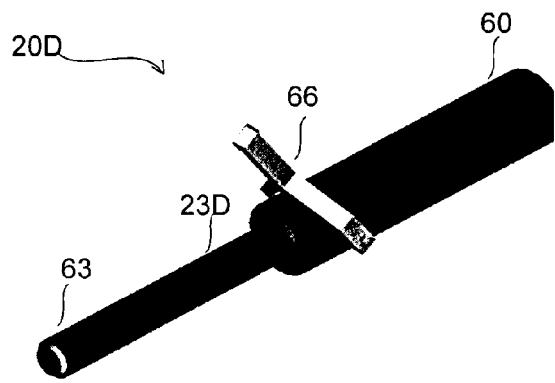

FIG. 3A, FIG. 3B, and FIG. 3C illustrate a stent mandrel fixture 20B in accordance with another embodiment of the invention. The stent mandrel fixture 20B is substantially similar to the stent mandrel fixture 20A except that the fixture 20B includes a substantially airtight inflatable cylinder or bladder 23B, which acts as a masking element to mask an inner surface of the stent 10 during a coating process, coupled to a pump 50 via a tube 52 in place of the tube 23A. As shown in FIG. 3C, which includes a cross section of the cylinder 23B, the cylinder 23B resembles a tire and comprises an outer diameter 54 and an inner diameter 56, and sidewalls which bound an interior airtight volume 55. The cylinder 23B includes a bore 57 formed by the inner diameter 56 through which the rod 24 travels.

The cylinder 23B can be fixed to the lock member 26 and/or nut 25, which act to prevent lateral movement of the cylinder 23B and stent 10 during a coating process. In addition, the lock member 26 and/or the nut 25 are rotationally mounted on the threaded rod 24, thereby enabling incremental positioning of the lock member 26 and the nut 25 with the cylinder 23B there between. In an alternative embodiment, the cylinder 23B is fixed to either the lock member 26 and/or the nut 25 and can act to seal the volume 55 if the cylinder 23B does not include sidewalls. In another embodiment of the invention, the diameter of the bore 57 is substantially equal to the outer diameter of the rod 24, thereby enabling a friction fit of the cylinder 23B onto the rod 24, which prevents unwanted lateral movement of the cylinder 23B during a coating process. Accordingly, the rod 24 need not be threaded and lock member 26 and nut 25 are not needed.

The interior volume 55 is in communication with the pump 50 via the tube 52. The pump 50 supplies gas or fluid to the interior volume 55 causing pressure to increase within the interior volume 55, thereby causing the outer diameter 54 to expand radially outwards from the rod 24, as shown in FIG. 5B. The supplied gas can have a temperature other than room temperature. The supplied gas, for example, can have a temperature between 35° C. and 80° C., to induce the evaporation of a solvent, preferably non-volatile solvents. Alternatively, the supplied gas can be cooler than 25° C. to retard the evaporation of the solvent, preferable retardation of the evaporation of unlike solvents.

In an embodiment of the invention, the inner diameter 56 is slightly larger than the diameter of the rod 24 while the outer diameter 54, in an unexpanded state, is less than the inner diameter of the stent 10, as positioned on the cylinder 23B. In one embodiment, the cylinder 23B has a length at least equal to the length of the stent 10, thereby enabling masking the entire length of the inner diameter of the stent 10. In another embodiment of the invention, the cylinder 23B is less than the length of the stent 10, thereby enabling masking of only a portion of the length of the inner diameter of the stent 10. The cylinder 23B is capable of expanding to at least the inner diameter of the stent 10 when the pump 50 pumps air into the interior area 55 of the cylinder 23B to increase the pressure within the cylinder 23B to, for example, 60–80 PSI. When the cylinder 23B is in an expanded state, the cylinder 23B acts to support the stent 10 and to mask the inner surface of the stent 10 (as shown in FIG. 5B) during a coating process so that the inner surface of the stent 10 is not coated with the same composition as the outer surface of the stent 10. In another embodiment of the invention, the sidewalls of the stent 10 can also be masked by the cylinder 23B as shown in FIG. 6A.

During operation of the stent mandrel fixture 20B, a stent 10 is loaded onto the fixture 20B by placing the stent 10 over the cylinder 23B when the cylinder 23B in an uncompressed state (FIG. 5A). The pump 50 then pumps gas into the interior area 55 of the cylinder 23B causing the outer diameter 54 of the cylinder 23B to expand radially outwards. In one embodiment of the invention, the cylinder 23B can expand radially outwards to substantially mask the inner surface of the stent 10, as shown in FIG. 5B. In another embodiment of the invention, the cylinder 23B can comprise a flexible and/or thin material, e.g., latex, and expands radially outwards to substantially mask the inner surface of the stent 10 as well as the sidewalls of the stent 10, as shown in FIG. 6A.

After the cylinder 23B is expanded radially outwards, a spray nozzle (not shown) sprays a composition onto the stent 10. As the inner diameter of the stent 10 is masked, only the sidewalls and outer diameter of the stent 10 are coated with a composition. In another embodiment of the invention, the sidewalls can also be masked and accordingly, only the outer surface of the stent 10 is coated with the composition.

After the coating of the stent 10, the pump 50 vents gas from within the interior volume 55, thereby lowering the pressure within the interior area 55 and enabling the tube 23B to return to a non-expanded state and further enabling removal of the stent 10 from the stent mandrel fixture 20B. The stent 10 can then have the inner surface coated via electroplating or spray coating.

FIG. 3D illustrates a stent mandrel fixture 20C in accordance with another embodiment of the invention. The fixture 20C, like the fixture 20B, is pneumatic-based. A cylinder 23C, for being placed through a bore of the stent 10, circumscribes a rod 24C. The cylinder 23C is an expandable tube having an inner volume constrained by the rod 24C. The rod 24C includes an inner bore and outlets 53 in fluid communication with the bore that feed gas, from the pump 50, into the interior volume of the cylinder 23C, thereby causing the cylinder 23C to expand radially outwards. The bore is in communication with a tube 59A, which is in communication with a coupling 58. The coupling 58 is in communication with the pump 50 via a tube 59B. Accordingly, gas from the pump 50 can travel through the tube 59B to and through the coupling 58 to and through the tube 59A to the rod 24C and through the outlets 53 into the interior volume of the cylinder 23C. The coupling 58 enables the rod 24C and cylinder 23C to rotate during a coating process without having to rotate the pump 50.

During a coating process, the pump 50 pumps air into the cylinder 23C thereby causing the cylinder 23C to expand to the inner diameter of the stent 10 (when the stent 10 is in an unexpanded state) thereby masking the inner diameter. In another embodiment of the invention, the cylinder 23C can expand past the inner diameter of the stent 10 to at least partially mask the sidewalls of the stent 10. After a coating process is complete, the pump 50 can vent gas from the interior region of the cylinder 23C, enabling it to return to its natural uncompressed state.

In an embodiment of the invention, the fixtures 20B and 20C can also include a pressure monitor disposed within the cylinder 23B or 23C. The pressure monitor can be coupled to feedback lines that provide the pump 50 with a measurement of pressure within the cylinder 23B or 23C so that the pump 50 can adjust the amount of gas pumped into the cylinder 23B or 23C.

FIG. 4A, FIG. 4B, FIG. 4C, and FIG. 4D illustrate a stent mandrel fixture 20D in accordance with another embodiment of the invention. The fixture 20D comprises a mandrel base 60 for receiving a rod 62; a tube or cylinder 23D that circumscribes the rod 62 and acts as a masking element to mask an inner surface of the stent 10 during a coating process; and a toggle switch 66 that is coupled to the rod 62, which acts as an expansion causing mechanism. In one embodiment of the invention, the mandrel base 60 is about 2 inches long with a diameter of about ⅜ of an inch and can be made of stainless steel.

The rod 62 has a disk 63 on the distal end. The rod 62 is coupled to the toggle switch 66 through a bore of the mandrel base 60 such that actuation of the switch 66 pulls the rod 62 further into the mandrel base 60, thereby pulling the disk 63 towards the mandrel base 60. The disk 63 laterally compresses the cylinder 23D against the mandrel base 60, thereby causing it to expand radially outwards. In one embodiment of the invention, the rod 62 is about 2.15 inches long with a diameter of about 0.28 inches and is made of stainless steel. The disk 63 of the rod 62 can also be made of stainless steel and have a diameter of about 0.55 inches with a width of 0.3 inches.

The cylinder 23D can be made of or coated with a non-stick material, such as TEFLON or low durometer PEBAX. The cylinder 23D circumscribes and is supported by the rod 62. The cylinder 23D is therefore constrained on both ends by the mandrel base 60 and the disk 63. Accordingly, when the cylinder 23D is compressed laterally between the mandrel base 60 and the disk 63, as is shown in FIG. 4B and FIG. 5B, the cylinder 23D is forced to expand outwards radially. In an embodiment of the invention, the cylinder 23D, in its uncompressed and unexpanded state, as shown in FIG. 4A and FIG. 5A, has an outer diameter of about 0.055 inches and an inner diameter of about 0.030 inches with a length of about 1.65 inches.

The toggle switch 66 changes the cylinder 23D between a compressed, expanded state and an uncompressed, non-expanded state. During operation of the stent mandrel fixture 20D, a stent 10 is loaded by placing it over cylinder 23D when the toggle switch 66 is placed in an open state as shown in FIG. 4A. The toggle switch 66 is then toggled to a closed or compressed state via an automated control or with human intervention as shown in FIG. 4B. The toggling of the toggle switch 66 pulls the rod 62 inwards towards the proximal end of the mandrel base 60, thereby pulling the disk 63 laterally inwards and compressing the cylinder 23D laterally, which causes the cylinder 23D to expand in a radial direction (i.e., the diameter of the cylinder 23D will increase) to mask the inner surface of the stent 10. The stent 10 can then be coated with a composition and dried while on the cylinder 23D. After application of the composition, the toggle switch 66 is moved to an open position, thereby decompressing the cylinder 23D so that the stent 10 can be released. As in all embodiments, the stent 10 can then be further dried in an oven until the solvent of the composition is evaporated.

Figure 5C:
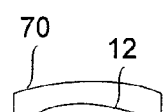
FIG. 5C illustrates a cross section of a stent strut after coating on the stent mandrel fixture of FIG. 2, FIG. 3, or FIG. 4.

FIGS. 5A and 5B illustrate cross sections of a stent mandrel fixture according to an embodiment of the invention. The stent mandrel fixture of FIG. 5A and FIG. 5B can include the embodiments shown in FIGS. 2A & 2B; FIG. 3A–3D; or FIG. 4A–4D. The stent mandrel fixture includes a masking element 23, such as the tube 23A or 23B, the masking element 23C, or the cylinder 23D having a bore within. The rod 24, 24C or rod 62 travels through the bore, thereby preventing the masking element 23 from expanding radially inwards when laterally compressed. When the masking element 23 is compressed laterally and expanded radially, as shown in FIG. 5B, the masking element 23 masks the inner surfaces 12C of the struts 12. Accordingly, during a coating process, only the exterior surface 12A and sidewalls 12B of the struts are coated with a composition leading to a coating 70 (FIG. 5C) on the exterior surface 12A and sidewalls 12B. A second coating (not shown) can be applied to the interior surfaces 12C via spraying, electroplating, or other conventional coating methods.

FIG. 6A illustrates a cross section of a stent mandrel fixture according to another embodiment of the invention. The stent mandrel fixture of FIG. 6A can include the embodiments shown in FIGS. 2A & 2B; FIG. 3A–3D; or FIG. 4A–4D. However, the masking element 23 is capable of partially or completely masking the sidewalls 12B in addition to the inner surfaces 12C. Accordingly, only the exterior surfaces 12A will be coated with a composition, forming a coating 72 (FIG. 6B), which can, for example, include a substantially pure drug composition. The masking element 23 can then be unexpanded to mask only the inner surfaces 12C as shown in FIG. 5B and a second coating applied, thereby forming coating 74 (FIG. 6C), which can include, for example, a substantially pure polymer. In an alternative embodiment, after applying the coating 72, the masking element 23 can be fully unexpanded, as shown in FIG. 5A, and then a coating applied, thereby encapsulating the coating 72 and all sides of the struts 12 with a coating 76 (FIG. 6D), which can include, for example, a substantially pure polymer. Advantages of the coatings applied as in FIGS. 6C and 6D include less coating on the stent 10 as only the exterior surfaces 12A are coated with a drug; encapsulation of the struts 12 prevents delamination or peeling at the edges of the struts 12; the encapsulating coating 74 or 76 can control drug release and have biocompatible properties; and drugs can be placed on the struts 12 where needed (e.g., a restenosis drug can placed solely on the exterior surfaces 12A, where it is needed), thereby preventing excessive use of the drug.

Figure 7:
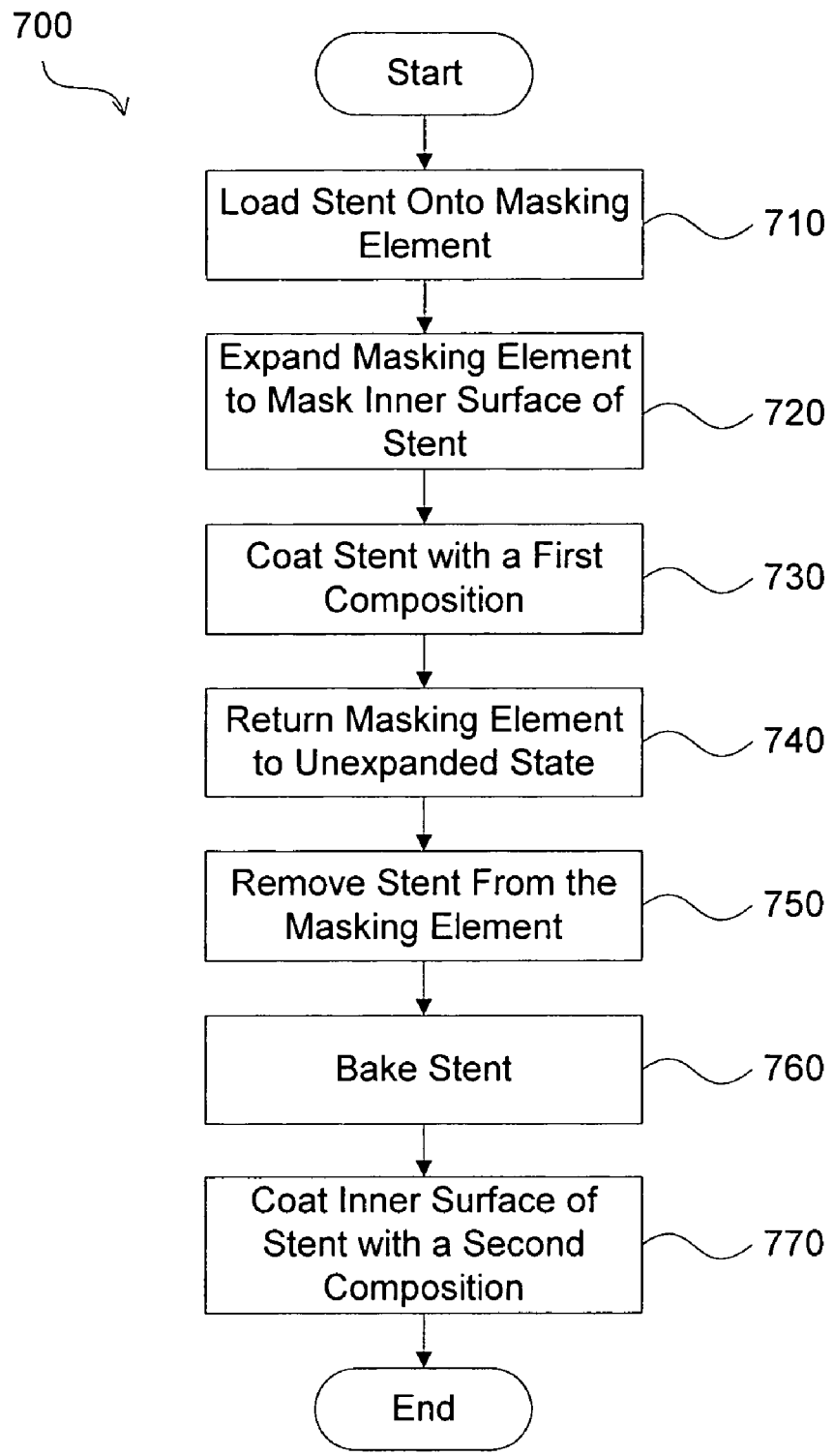
FIG. 7 illustrates a flowchart of a method of coating a stent using the stent mandrel fixture of FIG. 2, FIG. 3 or FIG. 4.

FIG. 7 illustrates a flowchart of a method 700 of coating a stent using the stent mandrel fixture 20A (FIG. 2A–FIG. 2B); 20B (FIG. 3A–FIG. 3D); or 20D (FIG. 4A–FIG. 4D). First, a stent 10 is loaded (710) over a masking element such as the tube 23A, or the cylinder 23B, 23C, or 23D (or other expandable masking element). The masking element is then expanded (720) until the masking element has an outer diameter at least equal to the inner diameter of the stent 10, thereby masking the inner surface of the stent 10. The expansion (720) can be invoked by an expansion causing mechanism such as the nut 25, the pump 50, or the toggle switch 66. In an alternative embodiment of the invention, the masking element can be further expanded to completely or partially cover the sidewalls in addition to the inner surface of the stent 10. The stent 10 is then coated (730) with a first composition. Due to the masking of at least the inner surface of the stent 10, only the outer surface and possibly the sidewalls (depending on how far the masking element is expanded) are coated (730) with the first composition. The masking element is then returned (740) to an unexpanded state and the stent 10 is removed (750) from the mandrel 24. The stent 10 is then baked (760) to remove solvent and so that the composition dries and hardens on the stent 10. The inner surface of the stent 10 is then coated (770), if desired, with a second composition having a therapeutic substance different from a therapeutic substance in the first composition. The coating (770) can be done via spraying or electroplating the composition. The method 700 then ends.

In another embodiment of the invention, in place of the removing (750) through the coating (770), the masking element can be unexpanded to less than the inner diameter of the stent 10 or up to the diameter of the stent 10 and then the stent 10 can be coated with a second composition (e.g., polymer) to encapsulate most or all of the surfaces of the stent 10. The stent 10 can then be removed from the masking element and baked to evaporate any solvent and to harden the coatings.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent support for supporting a stent during the application of a coating composition to the stent, comprising:

a hollow tubular member configured to be inserted into a longitudinal bore of a stent;

a rod extending through the tubular member; and a mechanism to cause the tubular member to expand and retract to support the stent during the application of a coating composition to the stent, wherein one end of the tubular member is attached to the rod and an opposing end of the tubular member is capable of being pushed by the mechanism towards the end of the tubular member attached to the rod, the mechanism being configured to push the opposing end of the tubular member to cause the tubular member to be laterally compressed and expand outwardly to engage an inner surface of the stent wherein the hollow tubular member is attached to the rod so as to define an enclosed space between the rod and the tubular member in which a fluid or gas can be supplied and contained, and wherein the mechanism comprises a pump for supplying a fluid or a gas into the space to expand the tubular member.

2. The support of claim 1, wherein the stent includes a frame structure having gaped regions, and wherein the hollow tubular member is configured to extend at least partially through the gaped regions.

3. A stent mandrel support, comprising:
  a masking element configured to be inserted through a bore of a stent, the masking element having an expanded configuration and a retracted configuration; and
  an expansion causing mechanism capable of expanding the masking element from the retracted configuration to the expanded configuration to cause the masking element to make contact with and mask an inner surface of the stent, wherein the expansion causing mechanism comprises
  a hollow rod in fluid communication with the masking element;
  a source for supplying a gas or fluid into the hollow rod to cause the masking element to expand;
  a rod supporting the masking element; and
  a lock member on the rod, the lock member acting to prevent lateral movement of the masking element.

4. The support of claim 3, wherein the expansion causing mechanism further comprises a gas or fluid line from the source in communication with the masking element.

5. The support of claim 3, wherein the expansion causing mechanism further comprises a pneumatic or hydraulic mechanism.

6. The support of claim 3, additionally including a coupler to allow the hollow rod to rotate while the source is kept in a stationary position.

7. A stent mandrel support, comprising:
  a masking element configured to be inserted through a bore of a stent, the masking element having an expanded configuration and a retracted configuration; and
  an expansion causing mechanism capable of expanding the masking element from the retracted configuration to the expanded configuration to cause the masking element to make contact with and mask an inner surface of the stent, wherein the expansion causing mechanism comprises
  a first member;
  a second member extending out from the first member, such that the masking element is positioned over the second member, the masking element having one end secured to the second member and an opposing end secured to the first member; and
  a toggle switch to drive the second member into the first member which causes lateral compression and radial expansion of the masking element.

* * * * *